(12) United States Patent
Carmeliet et al.

(10) Patent No.: US 7,226,908 B2
(45) Date of Patent: Jun. 5, 2007

(54) USE OF VEGF AND HOMOLOGUES TO TREAT NEURON DISORDERS

(75) Inventors: Peter Carmeliet, Landen (BE); Désiré Collen, Winksele (BE); Bert Oosthuyse, Horml (BE)

(73) Assignees: Vlaams Interuniversitair Instituut Voor Biotechnologie VZW, Ghent (BE); Collen Research Foundation VZW, Leuven (BE)

( * ) Notice: Subject to any disclaimer, the term of this patent is extended or adjusted under 35 U.S.C. 154(b) by 169 days.

(21) Appl. No.: 10/257,423

(22) PCT Filed: Apr. 12, 2001

(86) PCT No.: PCT/EP01/04293

§ 371 (c)(1),
(2), (4) Date: Oct. 10, 2002

(87) PCT Pub. No.: WO01/76620

PCT Pub. Date: Oct. 18, 2001

(65) Prior Publication Data

US 2003/0105018 A1 Jun. 5, 2003

(51) Int. Cl.
*A61K 38/18* (2006.01)
*C07K 14/475* (2006.01)

(52) U.S. Cl. ............ 514/12; 514/2; 530/399; 530/350

(58) Field of Classification Search ............ 424/198.1; 514/2; 530/300, 350, 399
See application file for complete search history.

(56) References Cited

U.S. PATENT DOCUMENTS

| | | | | |
|---|---|---|---|---|
| 5,332,671 A | * | 7/1994 | Ferrara et al. | 435/360 |
| 5,350,836 A | * | 9/1994 | Kopchick et al. | 530/399 |
| 6,455,283 B1 | * | 9/2002 | Ferrara et al. | 435/69.4 |

FOREIGN PATENT DOCUMENTS

| | | |
|---|---|---|
| WO | WO 98/31395 | 7/1998 |
| WO | WO 99/46364 | 9/1999 |
| WO | WO 99/47677 | 9/1999 |
| WO | WO 00/62798 | 10/2000 |

OTHER PUBLICATIONS

Miller, G. (2002). Breaking down barriers. Science 297:1116-1118.*
Pettit et al. (1998). The development of site-specific drug-delivery systems for protein and peptide biopharmaceuticals. Trends Biotechnol. 16:343-349.*
Lambrechts et al. (2004). VEGF: necessary to prevent motoneuron degeneration, sufficient to treat ALS? Trends in Molecular Medicine. 10(6):275-282.*
Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 492-495.*

Storkebaum et al. (2005). Treatment of motoneuron degeneration by intracerebroventricular delivery of VEGF in a rat model of ALS. Nature Neuroscience. 8(1):85-92.*
Jin et al., "Vascular endothelial growth factor: Direct neuroprotective effect in in vitro ischemia", 2000, PNAS 97:10242-10247.
Jin et al., "Vascular Endothelial Growth Factor Rescues HN33 Neural Cells from Death Induced by Serum Withdrawal", 2000, J. Mol. Neurosci.14:197-203.
Kilpatrick et al., "Molecular Mechanisms Regulating Motor Neuron Development and Degeneration", 1999, Mol. Neurobiol. 19:205-228.
Owens et al., "VEGF Promoter Polymorphisms and the Risk of Ischaemic Heart Disease", 2000, J. Amer. Coll. Cardiol. 35, suppl. A:306A.
Samii et al., "Vascular endothelial growth factor expression in peripheral nerves and dorsal root ganglia in diabetic neuropathy in rats", 1999, Neurosci. Lett. 3:159-162.
Schratzberger et al., "Favorable effect of VEGF gene transfer on ischemic peripheral neuropathy", 2000, Nature Med., 6:405-413.
Silverman et al., "Vascular, Glial and Neuronal Effects of Vascular Endothelial Growth Factor in Mesencephalic Explant Cultures", 1999, Neurosci. 90:1529-1541.
Soker et al., "Neuropilin-1 Is Expressed by Endothelial and Tumor Cells as an Isoform-Specific Receptor for Vascular Endothelial Growth Factor", 1998, Cell 92: 735-745.
Sondell et al., "Vascular Endothelial Growth Factor Has Neurotrophic Activity and Stimulates Axonal Outgrowth, Enhancing Cell Survival and Schwann Cell Proliferation in the Peripheral Nervous System", 1999, J. Neurosci. 19:5731-5740.
Chen, W et al., entitled "Lack of association of VEGF promoter polymorphisms with sporadic ALS," Neurology 2006;67; pp. 508-510.

* cited by examiner

*Primary Examiner*—Christine J. Saoud
*Assistant Examiner*—Jon M Lockard
(74) *Attorney, Agent, or Firm*—Amster, Rothstein & Ebenstein LLP

(57) ABSTRACT

The present invention relates to neurological and physiological dysfunction associated with neuron disorders. In (particular, the invention relates to the involvement of vascular endothelial growth factor (VEGF) and homologues in the aetiology of motor neuron disorders. The invention further concerns a novel, mutant transgenic mouse (VEGF$^{m/m}$) with a homozygous deletion in the hypoxia responsive element (HRE) of the VEGF promoter which alters the hypoxic upregulation of VEGF. These mice suffer severe adult onset muscle weakness due to progressive spinal motor neuron degeneration which is reminiscent of amyotrophic lateral sclerosis (ALS)—a fatal disorder with unknown aetiology. Furthermore, the neuropathy of these mice is not caused by vascular defects, but is due to defective VEGF-mediated survival signals to motor neurons. The present invention relates in particular to the isoform VEGF$_{165}$ which stimulates survival of motor neurons via binding to neuropilin-1, a receptor known to bind semaphorin-3A which is implicated in axon retraction and neuronal death, and the VEGF Receptor-2. The present invention thus relates to the usage of VEGF, in particular VEGF$_{165}$, for the treatment of neuron disorders and relates, in addition, to the usage of polymorphisms in the VEGF promotor for diagnosing the latter disorders.

16 Claims, 3 Drawing Sheets

SEQUENCE LISTING

```
<160> NUMBER OF SEQ ID NOS: 2

<210> SEQ ID NO 1
<211> LENGTH: 38
<212> TYPE: DNA
<213> ORGANISM: artificial sequence
<220> FEATURE:
<223> OTHER INFORMATION: forward primer

<400> SEQUENCE: 1
ttatcagaat tcattcccga ggcctgggga gagttggg                            38

<210> SEQ ID NO 2
<211> LENGTH: 34
<212> TYPE: DNA
<213> ORGANISM: artificial sequence
<220> FEATURE:
<223> OTHER INFORMATION: reverse primer

<400> SEQUENCE: 2
ataaagaatt cggaaggtca cagcccttcg gtgg                                34
```

USE OF VEGF AND HOMOLOGUES TO TREAT NEURON DISORDERS

CROSS-REFERENCES TO RELATED APPLICATIONS

Figure 1:
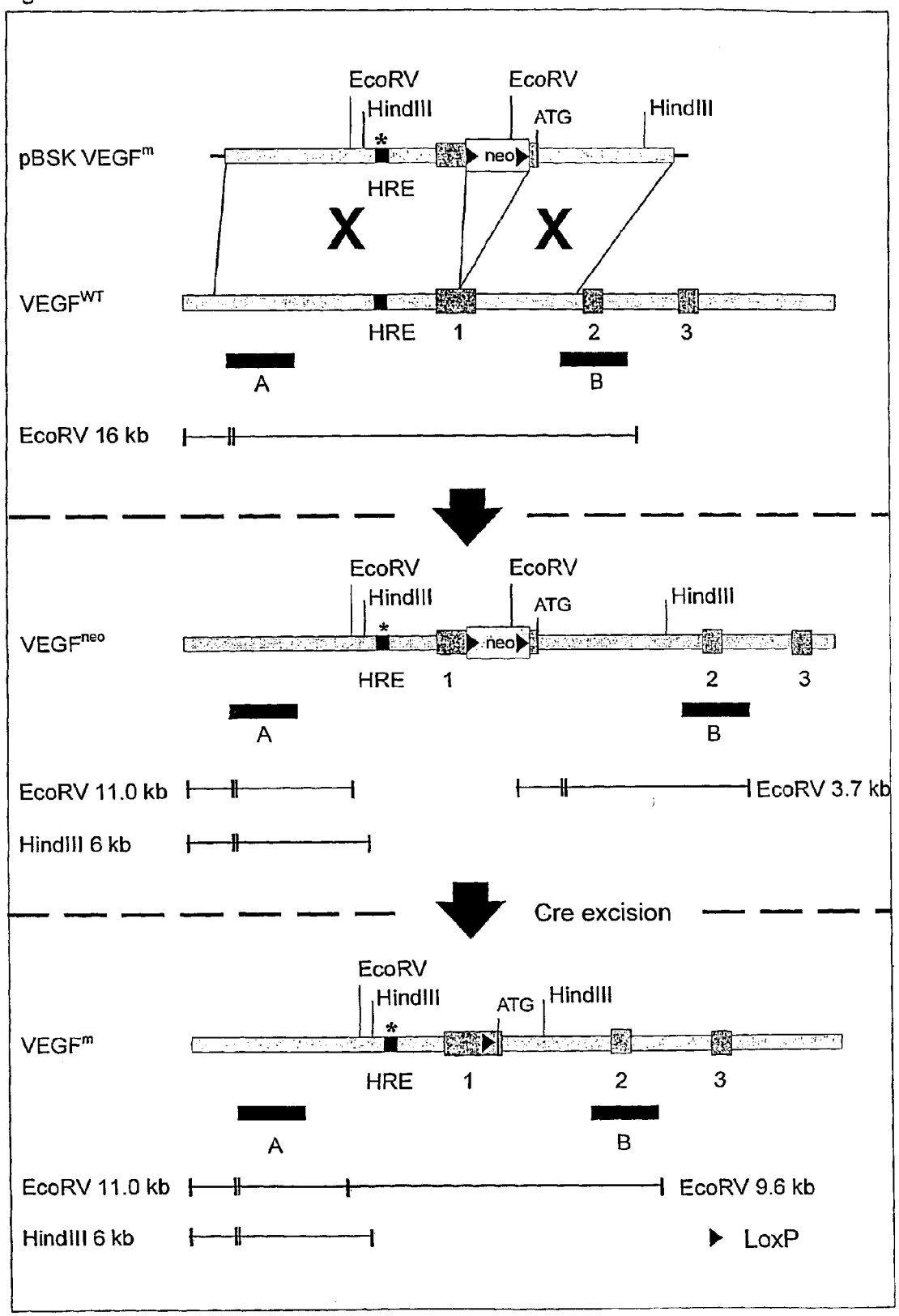

This application is a U.S. National Stage application under 35 U.S.C. 371 of PCT/EP01/04293, filed Apr. 12, 2001 which claims priority to European Patent Applications 00203382.7, filed Sep. 29, 2000, and 00201325.8, filed Apr. 12, 2000.

FIELD OF THE INVENTION

The present invention relates to neurological and physiological dysfunction associated with neuron disorders. In particular, the invention relates to the involvement of vascular endothelial growth factor (VEGF) and homologues in the aetiology of motor neuron disorders. The invention further concerns a novel, mutant transgenic mouse (VEGF$^{m/m}$) with a homozygous deletion in the hypoxia responsive element (HRE) of the VEGF promoter which alters the hypoxic upregulation of VEGF. These mice suffer severe adult onset muscle weakness due to progressive spinal motor neuron degeneration which is reminiscent of amyotrophic lateral sclerosis (ALS)—a fatal disorder with unknown aetiology. Furthermore, the neuropathy of these mice is not caused by vascular defects, but is due to defective VEGF-mediated survival signals to motor neurons. The present invention relates in particular to the isoform VEGF$_{165}$ which stimulates survival of motor neurons via binding to neuropilin-1, a receptor known to bind semaphorin-3A which is implicated in axon retraction and neuronal death, and the VEGF Receptor-2. The present invention thus relates to the usage of VEGF, in particular VEGF$_{165}$, for the treatment of neuron disorders and relates, in addition, to the usage of polymorphisms in the VEGF promotor for diagnosing the latter disorders.

BACKGROUND OF THE INVENTION

VEGF is a key player in the formation of new blood vessels (angiogenesis) during embryonic development as well as in a variety of pathological conditions[1,2]. Although VEGF primarily stimulates endothelial cells, it may also act on other cell types. Indeed, VEGF, VEGF receptor-1 (VEGFR-1/Flt1) and VEGF receptor-2 (VEGFR-2/KDR/Flk1) have recently been implicated in stroke[3,4], spinal cord ischemia[5], and in ischemic and diabetic neuropathy[6], WO 0062798. However, the latter molecules act predominantly via affecting vascular growth or function and a direct effect of VEGF on for example neuronal cells has not been shown[11,12]. Moreover, the in vivo relevance of such a direct effect is not validated.

Ischemia plays an essential role in the pathogenesis of neurological disorders, acutely during stroke and chronically during aging and several neurodegenerative disorders such as Alzheimer's disease, Parkinson's disease and Huntington disease. Neurons are particularly vulnerable to oxidative stress by free radicals (generated during ischemia/reperfusion) because of their high oxygen consumption rate, abundant lipid content, and relative paucity of antioxidant enzymes compared to other organs[16]. Cumulative oxidative damage due to a toxic gain of function of mutant Cu, Zn-superoxide dismutase (SOD1) participates in degeneration of motor neurons in a number of patients with familial amyotrophic lateral sclerosis (ALS)[17,18]. ALS affects 5 to 10 individuals per 100,000 people worldwide during the second half of their life, is progressive, usually fatal within 5 years after onset of symptoms, and untreatable[17-19]. Ninety to 95% of cases are sporadic. Although the mechanisms underlying sporadic ALS remain unknown, evidence suggests that oxidative injury, similar to that caused by SOD1 mutations, plays a pathogenetic role[18,20,21].

In response to hypoxia, 'survival' responses are initiated, including the production of stress hormones, erythropoietin, glycolytic enzymes and angiogenic molecules such as VEGF[22,23]. Hypoxia-inducible factors (HIFs) play an essential role in mediating this feedback response via binding to a defined hypoxia-response element (HRE) in the promotor of these genes[23]. Hypoxia is a predominant regulator of VEGF expression as induction of VEGF expression is rapid (minutes), significant (>10-fold) and responsive to minimal changes in oxygen[22,23]. Surprisingly, little attention has been paid to the possible role of hypoxia and HIFs in the initiation of feedback survival mechanisms in the nervous system. While several neurotrophic molecules have been identified[24,25], few have been shown to be regulated by hypoxia. In this regard, it remains unknown whether hypoxic regulation of VEGF provides neuroprotection, independently of its angiogenic activity.

Further in the nervous system, motor neurons are a well-defined, although heterogeneous group of cells responsible for transmitting information from the central nervous system to the locomotor system. Spinal motor neurons are specified by soluble factors produced by structures adjacent to the primordial spinal cord, signalling through homeodomain proteins. Axonal pathfinding is regulated by cell-surface receptors that interact with extracellular ligands and once synaptic connections have formed, the survival of the somatic motor neuron is dependent on the provision of target-derived growth factors, although non-target-derived factors, produced by either astrocytes or Schwann cells, are also potentially implicated. Somatic motor neuron degeneration leads to profound disability, and multiple pathogenetic mechanisms including aberrant growth factor signalling, abnormal neurofilament accumulation, excitotoxicity; autoimmunity have been postulated to be responsible. Even when specific deficits have been identified, for example, mutations of the superoxide dismutase-1 gene in familial amyotrophic lateral sclerosis and polyglutamine expansion of the androgen receptor in spinal and bulbar muscular atrophy, the mechanisms by which somatic mortor neuronal degeneration occurs remain unclear. In order to treat motor system degeneration effectively, we need to understand these mechanisms more thoroughly. Although it has been shown in the art that VEGF has neurotrophic actions on cultured mouse superior cervical ganglia and on dorsal root ganglia (Sondell M. et al. *Journal of Neuroscience*, (1999) 19, 5731), no studies are available about the possible role of VEGF on motor neurons. The present invention demonstrates that VEGF has a trophic role for neurons, in particular motor neurons, and unveils that defective hypoxic regulation of VEGF predisposes to neuron degeneration. Moreover, the present invention indicates that VEGF is a therapeutic agent for the treatment of motor neuron disorders and relates to the usage of polymorphisms in the VEGF promotor for diagnosing neuron disorders.

AIMS OF THE INVENTION

The present invention aims at providing research tools, diagnostics and therapeutics in order to improve the health and well-being of patients suffering from neural disorders. In particular, the present invention aims at providing the usage of VEGF, or homologues or fragments thereof, in order to treat patients suffering from Alzheimer disease, Parkinson's disease, Huntington disease, chronic ischemic brain disease, amyotrophic lateral sclerosis, amyotrophic lateral sclerosis-like diseases and other degenerative neuron, in particular motor neuron, disorders. More particularly, the present invention aims at providing the usage of $VEGF_{165}$ to prevent death of motor neurons in the spinal cord. The present invention also aims at providing receptors, such as neuropilin-1 and the vascular endothelial growth factor receptor-2 (VEGFR-2), which specifically bind to VEGF and which can be used to screen for other molecules binding to it. In other words, the present invention aims at providing therapeutics which stimulate survival of neurons or which inhibit death of neurons induced by, for example, semaphorin 3A. The present invention further aims at providing an animal which is characterized by having an altered (i.e. impaired or non-functional) hypoxia-induced VEGF expression compared to it's wild-type counterpart and which can be used as a research tool to screen for therapeutics as mentioned above. The present invention finally aims at providing polymorfisms in the VEGF promoter region, such as in the Hypoxia Responsive Element, which can be used to identify individuals prone to develop a neuron disorder or to treat neuron disorder patients via gene therapy.

FIGURE LEGENDS

FIG. 1: Targeting of the VEGF gene and muscle weakness in $VEGF^{m/m}$ mice.

Strategy to delete the HIF-1α binding-element in the VEGF promoter. The targeting vector $pBSK.VEGF^m$, the wild type ($VEGF^{WT}$) VEGF allele, the homologously recombined ($VEGF^{neo}$) VEGF allele, and the modified $VEGF^m$ allele after Cre-excision of the floxed neo cassette are shown. Probes are indicated by solid bars. HRE: hypoxia-response element to which HIF-1alfa binds; the asterisk and "m" denote the HRE deletion.

Figure 2:
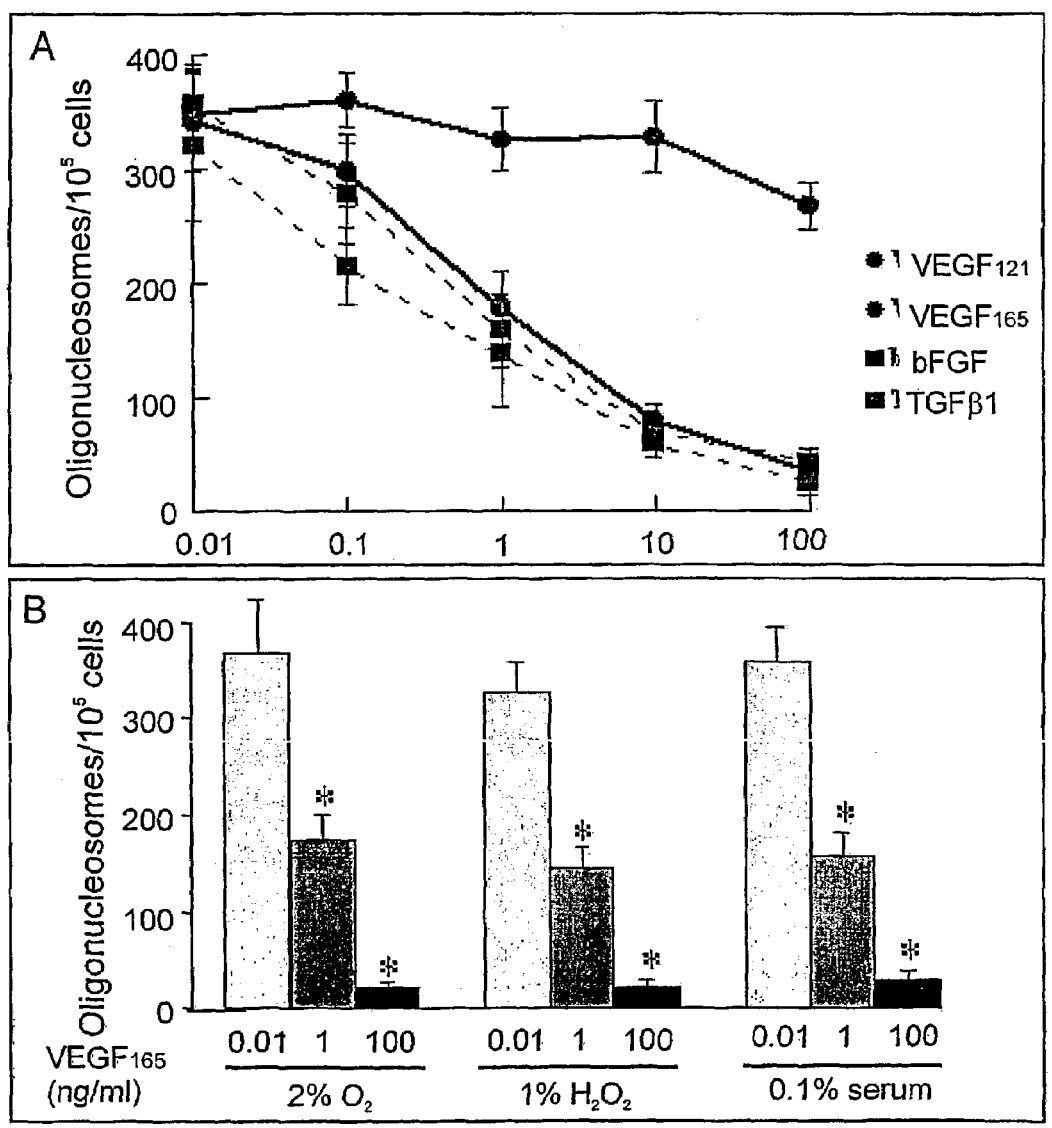
Figure 2:
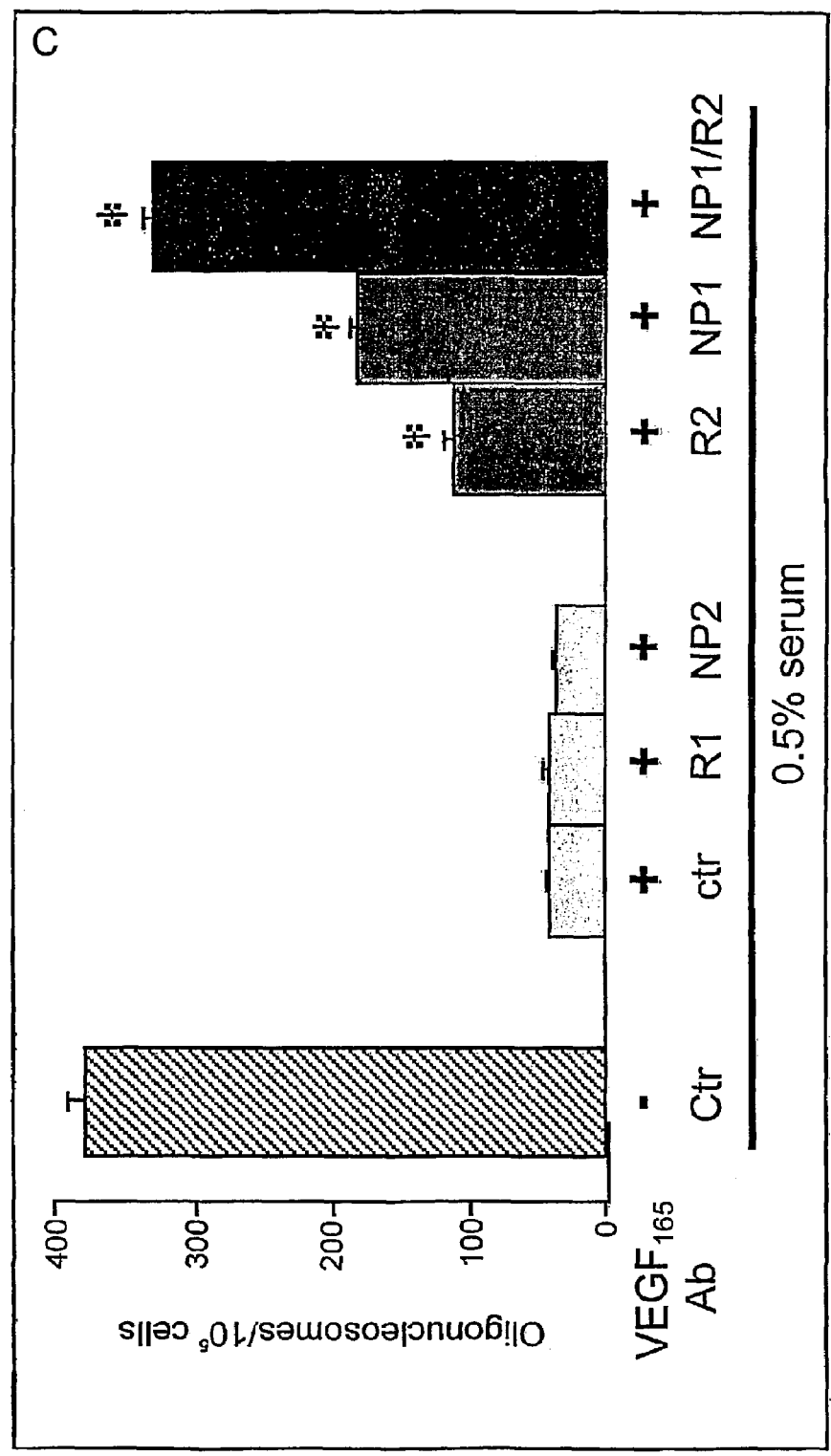

FIG. 2: Neurotrophic role of VEGF.

A, $VEGF_{165}$, but not $VEGF_{121}$, protects SCN34 motor neurons against apoptosis (quantified by oligonucleosomes) induced by TNF-alfa (50 ng/ml). The survival activity of $VEGF_{165}$ is comparable to that of bFGF or TGF-β1. B, $VEGF_{165}$ also protects SCN34 cells against apoptosis induced by hypoxia, $H_2O_2$, or serum deprivation. *: p<0.05 versus 0.01 ng/ml VEGF. C, The survival effect of $VEGF_{165}$ (100 ng/ml) is blocked by antibodies (Ab; 50 µg/ml) against VEGFR-2 (R2) and neuropilin-1 (NP1), but not to VEGFR-1 (R1), neuropilin-2 (NP2), or control (ctr) IgG's. Apoptosis was induced by serum starvation (0.5%). None of the antibodies modified the baseline level of apoptosis in the absence of VEGF. *: p<0.05 versus control IgG.

DETAILED DESCRIPTION OF THE INVENTION

The present invention shows that deletion of the hypoxia-response element in the VEGF promotor effectively abrogates hypoxic induction of VEGF. Based on the well-known role of VEGF in angiogenesis, it was anticipated that $VEGF^{m/m}$ mice would suffer impaired VEGF-mediated angiogenesis. Vascular defects do indeed appear to contribute to the lethality of $VEGF^{m/m}$ embryos but, surprisingly, there are no signs of vascular insufficiency in surviving $VEGF^{m/m}$ mice under baseline conditions. Furthermore, the neuropathy which is seen in adult $VEGF^{m/m}$ mice is also not due to vascular insufficiency because of the following findings: (i) the number, differentiation and ultrastructure of endothelial cells in the spinal cord, peripheral nerves and muscles of those mice are normal; (ii) endoneural perfusion is normal without signs of leakiness; (iii) pimonidazole staining of spinal cords after hypoxia is comparable with wt-mice; (iv) infarcts or microangiopathy, typically found in diabetic patients with ischemic neuropathy[47], are absent; (v) axonal lesions are not only present at the center (prone to ischemia), but also at the periphery of the nerves; (vi) degenerating motor neurons lay frequently in the immediate vicinity of normal capillaries; and (vii) other causes of ischemia including cardiac failure, anemia, or pulmonary insufficiency are excluded.

The present invention thus relates to a novel transgenic mouse model with an impaired hypoxic upregulation of VEGF and characterized by having a predisposition to adult onset progressive motor neuron degeneration with neuropathological features, reminiscent of amyotrophic lateral sclerosis. In this novel mouse model the neuropathy is not caused by vascular defects, but by deprivation of motor neurons from the neurotrophic effect of VEGF. It should be clear however that the present invention not only relates to a novel transgenic mouse, but also encompasses any non-human transgenic animal (such as a rat, dog, rabbit, non-human primate, etc.) which is characterized by having an impaired or non-functional hypoxia-induced VEGF expression compared to their wild-type counterparts. The present invention has significant medical implications. First, the genetic etiology of degenerative motor neuron disorders remains undetermined. In less than 2% of ALS cases, mutations in the SOD1 gene underlie the disease, but the pathogenesis of the remaining 98% remains unknown. Our findings indicate that abnormal gene regulation—not function—of VEGF constitutes a novel risk factor for motor neuron degeneration, and compels a search for genetic alterations that affect VEGF gene regulation. Even in ALS patients with a SOD1 mutation, genetically determined differences in VEGF gene regulation may explain the significant intrafamilial phenotypic variability. Second, there is no medical treatment for ALS to date. Our data demonstrate that VEGF has therapeutic value for motor neuron disorders. The availability of an animal model with characteristics of familial ALS (transgenic expression of mutant SOD1) provides an essential research tool. Our findings also indicate that $VEGF_{165}$ protect cortical neurons against N-methyl-D-aspartate. Third, the present $VEGF^{m/m}$ mouse model of adult onset motor neuron degeneration reflects several clinical and neuropathological features of ALS (progressive muscle atrophy due to degeneration of spinal motor neurons, characterized by neurofilament inclusions in the perikaryon and axonal swellings[17-19,32-34]). The $VEGF^{m/m}$ mouse is therefore a suitable model for evaluation of therapeutic strategies. Fourth, our data militate for caution against long-term use of VEGF-antagonists (currently being tested for treatment of cancer, diabetes, and rheumatoid arthritis), as they can predispose to motor neuron degeneration.

The present invention also indicates that VEGF, or homologues, derivates or fragments thereof, can be used to manufacture a medicament for the treatment of neuron disorders, and specifically for the treatment of neuronopathies and more specifically for the treatment of motor neuron disorders and even more specifically for the treatment of amyotrophic lateral sclerosis and amyotrophic lateral sclerosis-like diseases. In another embodiment VEGF, or homologues, derivates or fragments thereof, can be used to manufacture a medicament to prevent the death of motor neurons in the spinal cord. In a particular embodiment the VEGF$_{165}$-isoform can be used for the treatment of motor neuron disorders.

By 'neuron disorders' it is meant any physiological dysfunction or death of neurons present in the central nervous system. A non-limited list of such disorders comprises dementia, frontotemporal lobe dementia, Alzheimer's disease, Parkinson's disease, Huntington's disease, prion diseases, neuronopathies and motor neuron disorders. 'Neuronopathies' are characterized by neuronal cell death of motor neurons or sensory neurons and hence neuronopathies can be subdivided in motor and sensory neuron disorders. Motor Neuron Disease (MND) or motor neuron disorders is a group of diseases (disorders) involving the degeneration of the anterior horn cells, nerves in the central nervous system that control muscle activity. This leads to gradual weakening and eventually wasting of the musculature (atrophy). Diseases of the motor neuron are classified according to upper motor neuron (UMN) and/or lower motor neuron (LMN) involvement. Upper motor neurons originate in the brain, in particular, the motor cortex, and they synapse either directly or indirectly onto lower motor neurons. Upper motor neurons are more accurately referred to as pre-motor neurons, and they are responsible for conveying descending commands for movement. Lower motor neurons are divisable into two catergories: visceral and somatic motor neurons. Visceral motor neurons are autonomic pre-ganglionic neurons that regulate the activity of ganglionic neurons, which innervate glands, blood vessels, and smooth muscle. Somatic motor neurons innervate skeletal muscle and include first, anterior horn cells, which as the name implies, are located in the anterior horn of the spinal cord, and second, lower motor neurons located in the cranial nerve nuclei. Amyotrophic lateral sclerosis or ALS is the most frequent form (accounting for around 80% of all cases) of motor neuron disoreders. ALS is known as Lou Gehrig's disease, named after the famous Yankee baseball player. The initial symptoms of ALS are weakness in the hands and legs and often fasciculation of the affected muscles. Whichever limbs are affected first, all four limbs are affected eventually. Damage to the upper motor neurons produces muscle weakness, spasticity and hyperactive deep tendon reflexes. Lower motor neuron damage produces muscle weakness with atrophy, fasciculations, flaccidity and decreased deep tendon reflexes. ALS has features of both upper and lower motor neurons of the cranial nerves, therefore symptoms are isolated to the head and neck. Some patients will also display UMN involvement of the cranial nerves and if this is the sole manifestation it is referred to as Pseudobulbar pulsy. Spinal muscular atrophy or progressive muscular atrophy is a MND that does not involve the cranial nerves and is due to lower motor neuron degeneration. Shy-Drager syndrome is characterized by postural hypotension, incontinence, sweating, muscle rigidity and tremor, and by the loss of neurones from the thoracic nuclei in the spinal cord from which sympathetic fibres originate. Destructive lesions of the spinal cord result in the loss of anterior horn cells. This is seen in myelomeningocele and in syringomyelia, in which a large fluid-filled cyst forms in the centre of the cervical spinal cord. Poliomyelitis virus infection also destroys anterior horn cells. Spinal cord tumours may locally damage anterior horn cells either by growth within the cord (gliomas) or by compression of the spinal cord from the outside (meningiomas, schwannomas, metastatic carcinoma, lymphomas).

Dorsal root ganglion cells may be damaged by herpex simplex and varicella-zoster viruses. Such infections are associated with a vesicular rash in the skin regions supplied by those neurones. A similar loss of sensory neurones is observed in ataxia telangiectasia, a disorder associated with progressive cerebellar ataxia and symmetrical telangiectases of the skin and conjunctiva. Neuronal loss from autonomic ganglia is observed in amyloid neuropathies and in diabetes.

A normal number of capillaries developed in VEGF$^{m/m}$ skeletal muscle, but their lumen size was reduced. Irrespective of whether the smaller capillaries were the cause or consequence of the reduced muscle growth, oxygenation was normal and there were no signs of ischemia in VEGF$^{m/m}$ muscle, indicating that perfusion matched the metabolic demands of the muscle fibers. VEGF is able to induce vasodilation which could result in structural vascular remodeling (Laitinen M. et al. (1997) *Hum Gene Ther* 8, 1737) but VEGF levels in normoxic and hypoxic VEGF$^{m/m}$ muscle were normal. The normal VEGF and reduced IGF-1 levels may suggest that growth of muscle fibers and not of vessels was primarily affected. In contrast, neuronal perfusion was reduced by 50% in VEGF$^{m/m}$ mice, despite a normal number, size and differentiation of the capillaries, and a normal hypercapnic vasoreactive response. Why perfusion is reduced in some but not in other organs in VEGF$^{m/m}$ mice and whether these organ-specific perfusion deficits relate to the variably reduced baseline and hypoxic VEGF levels in these organs remain to be determined. In contrast to skeletal muscle where the vasculature expands almost 10-fold, the neuronal vascular network expands less but primarily remodels after birth (Feher G. et al. (1996) *Brain Res Dev Brain Res* 91, 209). VEGF has been implicated in the remodeling of the primitive (poorly perfused) capillary plexus at birth to a functionally perfused vasculature in the adult (Ogunshola et al. (2000) *Brain Res Dev Brain Res* 119, 139). An intriguing question is therefore whether the reduced neuronal VEGF levels in VEGF$^{m/m}$ mice reduced neuronal perfusion via impaired vascular remodeling. Irrespective of the mechanism, the neuronal hypoperfusion in VEGF$^{m/m}$ mice might have contributed to the stunted growth and infertility, for instance by impairing secretion of hypothalamic factors. Mice with hypothalamic or pituitary defects are smaller and sterile (Chandrashekar V. et al. (1996) *Biol Reprod* 54, 1002). The reduced IGF-1 plasma levels are consistent with such hypothesis.

While a reduction of neuronal perfusion by 50% did not predispose VEGF$^{m/m}$ mice to neuronal infarcts, it likely caused chronic neuronal ischemia. Animal models of chronic spinal cord ischemia are not available, but acute spinal cord ischemia causes significant motor neuron degeneration (Lang-Lazdunski, L. et al. (2000) *Stroke* 31, 208). Surgically induced cerebral perfusion deficits caused cognitive defects but spared rats from motoric dysfunction, and variably caused histologic signs of neuronal loss (Ohta H. et al (1997) *Neuroscience* 79, 1039). An animal model of spontaneous chronic neuronal ischemia is, however, not available. Thus, in a specific embodiment the invention provides a model for chronic spinal cord ischemia.

The VEGF$^{m/m}$ mouse model promises to be fruitful for studying the consequences of neuro-vascular insufficiency on cognitive function and on the progression of neurodegenerative disorders. In a specific embodiment the invention provides a model for cognitive dysfunction and in another specific embodiment the VEGF$^{m/m}$ mouse model is useful to breed with current mouse models known in the art for neurodegenerative disorders, for example models for Alzheimer's Disease (Bornemann et al. (2000) *Ann NY Acad Sci* 908, 260, Van Leuven F. (2000) *Prog Neurobiol* 61, 305, Sommer B. et al. (2000) *Rev Neurosci* 11, 47).

A diminished nervous blood flow in the brain can lead to brain ischemia. Brain ischemia is a process of delayed neuronal cell death and not an instantaneous event. A diminished cerebral blood flow initiates a series of events (the "ischemic cascade") that can lead to cell destruction. The goal of neuroprotection is to intervene in the process that ischemic neurons undergo as part of the final common pathway of cell death. The ischemic cascade has been intensively studied, and although it has not been completely delineated, certain reproducible aspects are recognized. The normal amount of perfusion to human brain gray matter is 60 to 70 mL/100 g of brain tissue/min. When perfusion decreases to <25 mL/100 g/min, the neuron is no longer able to maintain aerobic respiration. The mitochondria are forced to switch over to anaerobic respiration, and large amounts of lactic acid are generated. This metabolic by-product accumulates in the extracellular regions and causes a local change in the pH level. This fundamental change in the environment surrounding ischemic cells has been confirmed in humans by magnetic resonance spectroscopy and by single photon emission computed tomography (SPECT). Many studies have focussed on stroke as a model for brain ischemia. However, recently chronic reductions in cerebral blood flow have been observed to be associated with aging and progressive neurodegenerative disorders which can precipitate cognitive failure (Bennet et al. (1998) Neuroreport 9, 161). For example regional cerebral blood flow abnormalities to the frontal and temporal regions are observed in depressed patients with cognitive impairment (Dolan et al. (1992) J Neurol Neurosurg Psychiatry 9, 768, Ritchie et al. (1999) Age Ageing 28, 385). In Alzheimer's disease (AD), an example of a neurodegenerative disorder, an impaired cerebral perfusion originates in the microvasculature which affects the optimal delivery of glucose and oxygen and results in a breakdown of metabolic pathways in brain cells such as in the biosynthetic and synaptic pathways. It is proposed that two factors need to be present before cognitive dysfunction and neurodegeneration is expressed in AD brain, advanced aging, and the presence of a specific condition that further lowers cerebral perfusion (de la Torre (1999) Acta Neuropathol 98, 1). Further in AD a critical threshold cerebral hypoperfusion is a self-perpetuating, contained and progressive circulatory insufficiency that will destabilize neurons, synapses, neurotransmission and cognitive function, creating in its wake a neurodegenerative process characterized by the formation of senile plaques, neurofibrillary tangles and amyloid angiopathy.

Cognition is referred to the process involved in knowing, or the act of knowing, which in its completeness includes perception and judgement. Cognition includes every mental process that can be described as an experience of knowing as distinguished from an experience of feeling or of willing. It includes, in short, all processes of consciousness by which knowledge is built up, including perceiving, recognizing, conceiving, and reasoning. The essence of cognition is judgement, in which a certain object is distinguished from other objects and is characterized by some concept or concepts. Cognitive disorders or cognitive dysfunction are disturbances in the mental process related to cognition. An overview of cognitive disorders (also called amnestic disorders) can be found in the Diagnostic and Statistical Manual of Mental Disorders (DSM-IV™) (ISBN 0890420629).

In a specific embodiment the novel VEGF$^{m/m}$ mouse model can be used to identify and/or to test molecules to prevent and/or to treat neuronal ischemia or neurodegenerative disorders and/or cognitive dysfuntion.

In another embodiment the present invention further indicates that VEGF, or homologues, derivatives or fragments thereof, can be used for the manufacture or a medicament to prevent and/or to treat neuronal ischemia such as brain ischemia. And in yet another embodiment VEGF, or homologues, derivatives or fragments thereof, can be used for the manufacture or a medicament to prevent and/or to treat cognitive dysfunction.

VEGF and homologues such as VEGF-B, VEGF-C, VEGF-D and PLGF are described in detail in Neufeld G. et al, Faseb Journal, 13, 9-22, 1999, Korpelainen E. I. et al, Curr. Opin. Cell. Biol. 10, 159-164, 1998 and in Joukov, V. et al. J. Cell. Physiol. 173, 211-215, 1997. In particular, certain of the VEGF genes, homologues, fragments, and derivatives thereof that are useful for practicing the claimed invention are described in GenBank Accession Nos. NM 003376 ("Homo sapiens vascular endothelial growth factor (VEGF) mRNA"); NM 003377 ("Homo sapiens vascular endothelial growth factor B (VEGFB) mRNA"); NM 005429 ("Homo sapiens vascular endothelial growth factor C (VEGFC) mRNA"); NM 004469 ("Homo sapiens c-fos induced growth factor (vascular endothelial growth factor D) (FIGF) mRNA); AF 024710 ("Homo sapiens vascular growth factor (VEGF$_{165}$)) mRNA, 3'UTR, mRNA sequence"); and U.S. Pat. No. 6,013,780 ("VEGF$_{145}$ expression vectors"); U.S. Pat. No. 5,935,820 ("Polynucleotides encoding vascular endothelial growth factor 2"); U.S. Pat. No. 5,607,918 ("vascular endothelial growth factor-B and DNA coding therefore"). The preferred nucleic acids of the invention encode the above-mentioned angiogenic growth factor polypeptides, as well as their homologues and alleles and functionally equivalent fragments or variants of the foregoing. For example, human VEGF 1 (VEGF A) exists in four principal isoforms, phVEGF$_{121}$; phVEGF$_{145}$; phVEGF$_{165}$; and phVEGF$_{189}$. Preferably, the VEGF nucleic acid has the nucleotide sequence encoding an intact human angiogenic growth factor polypeptide, i.e., the complete coding sequence of the gene encoding a human VEGF; however the invention also embraces the use of nucleic acids encoding fragments of an intact VEGF.

Homologues and alleles of the nucleic acid and amino acid sequences reported for the VEGF genes, such as those mentioned herein, also are also within the scope of the present invention. In addition, nucleic acids of the invention include nucleic acids which code for the VEGF polypeptides having the sequences reported in the public databases and/or literature, but which differ from the naturally occurring nucleic acid sequences in codon sequence due to the degeneracy of the genetic code. The invention also embraces isolated functionally equivalent fragments, variants, and analogs of the foregoing nucleic acids; proteins and peptides coded for by any of the foregoing nucleic acids; and complements of the foregoing nucleic acids. 'Functionally' means that the fragments, variants and analogs must have the capacity to treat a neuron disorder and in particular a motor neuron disorder.

The term 'derivatives' refers to any variant, mutant or peptide composition of VEGF, which retains the capacity, or can be used, to treat degenerative motor neuron disorders as defined above. The latter term also includes post-translational modifications of the amino acid sequences of VEGF such as glycosylation, acetylation, phosphorylation, modifications with fatty acids and the like. Included within the definition are, for example, amino acid sequences containing one or more analogues of an amino acid (including unnatural amino acids), amino acid sequences with substituted linkages, peptides containing disulfide bonds between cysteine residues, biotinylated amino acid sequences as well as other modifications known in the art. The term thus includes any protein or peptide having an amino acid residue sequence substantially identical to a sequence specifically shown herein in which one or more residues have been conservatively substituted with a biologically equivalent residue. Examples of conservative substitutions include the substitution of one-polar (hydrophobic) residue such as isoleucine, valine, leucine or methionine for another, the substitution of one polar (hydrophilic) residue for another such as between arginine and lysine, between glutamine and asparagines, between glycine and serine, the substitution of one basic residue such as lysine, arginine or histidine for another, or the substitution of one acidic residue, such as aspartic acid or glutamic acid for another. The phrase "conservative substitution" also includes the use of a chemically derivatized residue in place of a non-derivatized residue provided that the resulting protein or peptide is biologically equivalent to the protein or peptide of the invention.

'Chemical derivative' refers to a protein or peptide having one or more residues chemically derivatized by reaction of a functional side group. Examples of such derivatized molecules, include but are not limited to, those molecules in which free amino groups have been derivatized to form amine hydrochlorides" p-toluene sulfonyl groups, carbobenzoxy groups, t-butyloxycarbonyl groups, chloracetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those proteins or peptides, which contain one or more naturally-occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine; and ornithine may be substituted for lysine. The proteins or peptides of the present invention also include any protein or peptide having one or more additions and/or deletions or residues relative to the sequence of a peptide whose sequence is shown herein, so long as the peptide is biologically equivalent to the proteins or peptides of the invention. When percentage of sequence identity is used in reference to polypeptides (i.e. homologues), it is recognized that residue positions which are not identical often differ by conservative aa substitutions, where aa residues are substituted for other aa residues with similar chemical properties (for example charge or hydrophobicity) and therefore do not change the functional properties of the polypeptide. Where sequences differ in conservative substitutions, the percent sequence identity may be adjusted upwards to correct for the conservative nature of the substitution. Means for making this adjustment are well known to those skilled in the art. Typically this involves scoring a conservative substitution as a partial rather than a full mismatch, thereby increasing the percentage sequence identity. Thus, for example (and as described in WO 97/31116 to Rybak et al.), where an identical aa is given a score of 1 and a non-conservative substitution is given a score of zero, a conservative substitution is given a score between zero and 1. In this regard, it should be clear that polypeptides, or parts thereof, comprising an aa sequence with at least 55%, preferably 75%, more preferably 85% or most preferably 90% sequence identity with the amino acid sequence of VEGF, or parts thereof, fall within the scope of the present invention. It should also be clear that polypepuides which are immunologically reactive with antibodies raised against VEGF, or parts thereof, fall within the scope of the present invention.

The term 'fragments of VEGF' refers to any fragment, including any modification of said fragment as described above, which retains the capacity, or can be used, to treat neuron disorders and in particular motor neuron disorders.

The terms 'pharmaceutical composition' or 'medicament' or 'use for the manufacture of a medicament to treat' relate to a composition comprising VEGF or homologues, derivatives or fragments thereof as described above and a pharmaceutically acceptable carrier or excipient (both terms can be used interchangeably) to treat diseases as indicated above. Suitable carriers or excipients known to the skilled man are saline, Ringer's solution, dextrose solution, Hank's solution, fixed oils, ethyl oleate, 5% dextrose in saline, substances that enhance isotonicity and chemical stability, buffers and preservatives. Other suitable carriers include any carrier that does not itself induce the production of antibodies harmful to the individual receiving the composition such as proteins, polysaccharides, polylactic acids, polyglycolic acids, polymeric amino acids and amino acid copolymers. The 'medicament' may be administered by any suitable method within the knowledge of the skilled man. The preferred route of administration is parenterally. In parental administration, the medicament of this invention will be formulated in a unit dosage injectable form such as a solution, suspension or emulsion, in association with the pharmaceutically acceptable excipients as defined above. However, the dosage and mode of administration will depend on the individual. Generally, the medicament is administered so that the protein, polypeptide, peptide of the present invention is given at a dose between 1 µg/kg and 10 mg/kg, more preferably between 10 µg/kg and 5 mg/kg, most preferably between 0.1 and 2 mg/kg. Preferably, it is given as a bolus dose. Continuous infusion may also be used and includes continuous subcutaneous delivery via an osmotic minipump. If so, the medicament may be infused at a dose between 5 and 20 µg/kg/minute, more preferably between 7 and 15 µg/kg/minute.

In a particularly preferred embodiment the infusion with a composition comprising VEGF or homologues, derivatives or fragments thereof is intrathecal. Intrathecal administration can for example be performed by means of surgically implanting a pump and running a catheter to the spine. It should be mentioned that intrathecal administration of VEGF or homologues, derivatives or fragments thereof is a particularly important aspect of the present invention. Indeed, since we have shown that VEGF has a neurotrophic aspect on neurons and more particularly on motor neurons, intrathecal administration is a preferred way. This is in contrast with WO 0062798 were therapeutic angiogenesis is aimed at in order to treat ischemic peripheral neuropathy.

Instead of delivering VEGF or a homologue, derivative or fragment thereof, as a protein to a patient in need for treatment of a neuron disorder or more particularly a motor neuron disorder, also a nucleic acid encoding VEGF, or a homologue, derivative or fragment thereof can be delivered to said patient. In that case the nucleic acid encoding VEGF or homologue, derivative or fragment thereof, can be operatively coupled to a promoter that can express said angiogenic growth factor in a target cell (e.g., an endothelial cell, a nerve cell, a muscle cell, a neuron, a motor neuron). Often the nucleic acid is contained in an appropriate expression vector (e.g., plasmid, adenoviral vector, modified adenoviral vector, retroviral vector, liposome) to more efficiently genetically modify the target cell and achieve expression of said angiogenic growth factor. For example, in WO 9831395 the selective transfer of genes into motor neurons is fully described.

In another embodiment of the invention it is shown that the $VEGF_{165}$ isoform, but not the $VEGF_{121}$ isoform, provides neuroprotection via binding to neuropilin-1 and VEGFR-2.

In yet another embodiment of the invention inhibitors of Sema3A, a molecule which is implicated in neuronal apoptosis[43] and axon retraction[44], and inhibits binding of $VEGF_{165}$ to neuropilin-1[9], can be made and used for the treatment of neuron disorders. Neuropilin-1 also binds Sema3A, implicated in repulsion of motor projections during development[11-15]. Neuropilin-1 and Sema3A are expressed in the ventral horn after birth, but their role has remained enigmatic. A recent in vitro study suggested a role for Sema3A in apoptosis of sympathetic and cerebellar neurons[43], whereas downregulation of Sema3A was suggested to be a prerequisite for axonal regeneration after nerve injury[44].

In yet another embodiment VEGF, or homologues, derivatives or fragments thereof can be administered for the prevention of neuronal loss or more specifically of motor neuronal loss in the spinal cord in for example surgical indications where an ischemic insult to neurons or motor neurons can be expected. The initiation of neuroprotective pathways during hypoxia is required, as these vital post-mitotic motor neurons cannot regenerate after a lethal hypoxic insult. In this regard only a few neuroprotective molecules such as NGF, bFGF, TGFβ1[52-54] have been characterized. The present invention clearly indicates that VEGF is a potent neuroprotective agent, as regulation of its expression by hypoxia is rapid (minutes), significant (>10-fold) and sensitive to small changes in oxygen. The absence of neuroprotective VEGF responses in $VEGF^{m/m}$ mice—even though they might only occur transiently, but repetitively—may explain why motor neurons in these mice ultimately degenerate after cumulative sublethal mini-insults of hypoxia.

Neuropilin-1 (NP-1), a receptor for the $VEGF_{165}$ isoform[9,10] and for the neurorepellant semaphorin 3A (Sema3A)[11-13] is shown to be essential for guiding neuronal projections during embryonic patterning[11-15]. However, it is not known if NP-1 and/or Sema3A have any role in neuronal function after birth. In a further embodiment the invention further provides methods for identifying compounds or molecules which bind on the neuropilin receptor and VEGFR-2 and stimulate the survival of neurons and more particularly motor neurons. In this invention the results show that $VEGF_{165}$, via binding to neuropilin-1 and VEGFR-2, mediates survival of NSC34 motor neurons. Both receptors are expressed on motor neurons in adult spinal cords in vivo, and are therefore accessible to $VEGF_{165}$, produced by the motor neuron itself or by other nearby cells. Neuropilin-1 and VEGFR-2 act as co-receptors in stimulating endothelial cell motility[9,10] and also cooperate in mediating neuronal survival. These methods are also referred to as 'drug screening assays' or 'bioassays' and typically include the step of screening a candidate/test compound or agent for the ability to interact with (e.g. bind to) neuropilin-1 and VEGFR-2. Candidate compounds or agents, which have this ability, can be used as drugs to treat degenerative disorders. Candidate/test compounds such as small molecules, e.g. small organic molecules, and other drug candidates can be obtained, for example, from combinatorial and natural product libraries.

The invention also provides methods for identifying compounds or agents which can be used to treat degenerative neurons. These methods are also referred to as 'drug screening assays' or 'bioassays' and typically include the step of screening a candidate/test compound or agent for the ability to interact with (e.g., bind to) neuropilin-1 and VEGFR-2. Candidate/test compounds or agents which have this ability, can be used as drugs to treat degenerative neuron disorders. Candidate/test compounds such as small molecules, e.g., small organic molecules, and other drug candidates can be obtained, for example, from combinatorial and natural product libraries. In one embodiment, the invention provides assays for screening candidate/test compounds which interact with (e.g., bind to) neuropilin-1 and VEGFR-2. Typically, the assays are cell-free assays which include the steps of combining neuropilin-1 and VEGFR-2 and a candidate/test compound, e.g., under conditions which allow for interaction of (e.g. binding on the candidate/test compound with neuropilin-1 and VEGFR-2 to form a complex, and detecting the formation of a complex, in which the ability of the candidate compound to interact with neuropilin-1 and VEGFR-2 is indicated by the presence of the candidate compound in the complex. Formation of complexes between the neuropilin-1 and the candidate compound can be quantitated, for example, using standard immunoassays. The neuropilin-1 employed in such a test may be free in solution, affixed to a solid support, borne on a cell surface, or located intracellularly. In another embodiment, the invention provides screening assays to identify candidate/test compounds which stimulate neuropilin-1 and VEGFR-2 or inhibit binding of sema3A to neuropilin-1 and/or VEGFR-2. Typically, the assays are cell-free assays which include the steps of combining neuropilin-1 and VEGFR-2 of the present invention or fragments thereof, and a candidate/test compound, e.g., under conditions wherein but for the presence of the candidate compound, the neuropilin-1 and, VEGFR-2 or a biologically active portion thereof interacts with (e.g., binds to) the target molecule or the antibody, and detecting the formation of a complex which includes the neuropilin-1 and the target molecule or the antibody, or detecting the interaction/reaction of neuropilin-1 and the target molecule or antibody. Detection of complex formation can include direct quantitation of the complex.

To perform the above described drug screening assays, it is feasible to immobilize neuropilin-1 and VEGFR-2 or its (their) target molecule(s) to facilitate separation of complexes from uncomplexed forms of one or both of the proteins, as well as to accommodate automations of the assay. Interaction (e.g., binding of of neuropilin-1 and VEGFR-2 to a target molecule can be accomplished in any vessel suitable for containing the reactants. Examples of such vessels include microtitre plates, test tubes, and microcentrifuge tubes. In one embodiment, a fusion protein can be provided which adds a domain that allows the protein to be bound to a matrix. For example, neuropilin-1-His tagged can be adsorbed onto Ni-NTA microtitre plates (Paborsky et al., 1996), or neuropilin-1-ProtA fusions adsorbed to IgG, which are then combined with the cell lysates (e.g., $^{35}$S-labeled) and the candidate compound, and the mixture incubated under conditions conducive to complex formation (e.g., at physiological conditions for salt and pH). Following incubation, the plates are washed to remove any unbound label, and the matrix immobilized and radiolabel determined directly, or in the supernatant after the complexes are dissociated. Alternatively, the complexes can be dissociated from the matrix, separated by SDS-PAGE, and the level of neuropilin-1 binding protein found in the bead fraction quantitated from the gel using standard electrophoretic techniques. Other techniques for immobilizing protein on matrices can also be used in the drug screening assays of the invention. For example, either neuropilin-1 and VEGFR-2 or its target molecules can be immobilized utilizing conjugation of biotin and streptavidin. Biotinylated neuropilin-1 and VEGFR-2 can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with neuropilin-1 but which do not interfere with binding of the protein to its target molecule can be derivatized to the wells of the plate, and neuropilin-1 and VEGFR-2 trapped in the wells by antibody conjugation. As described above, preparations of a neuropilin-1-binding protein and a candidate compound are incubated in the neuropilin-1-presenting wells of the plate, and the amount of complex trapped in the well can be quantitated. Methods for detecting such complexes, in addition to those described above for the GST-immobilized complexes, include immunodetection of complexes using antibodies reactive with the neuropilin-1 target molecule and VEGFR-2-target molecule, or which are reactive with neuropilin-1 and VEGFR-2 and compete with the target molecule; as well as enzyme-linked assays which rely on detecting an enzymatic activity associated with the target molecule. Another technique for drug screening which provides for high throughput screening of compounds having suitable binding affinity to neuropilin-1 and VEGFR-2 is described in detail in. "Determination of Amino Acid Sequence Antigenicity" by Geysen H N, WO 84103564, published on Sep. 13, 1984. In summary, large numbers of different small peptide test compounds are synthesized on a solid substrate, such as plastic pins or some other surface. The protein test compounds are reacted with fragments of neuropilin-1 or/and VEGFR-2 and washed. Bound neuropilin-1 is then detected by methods well known in the art. Purified neuropilin-1 or/and VEGFR-2 can also be coated directly onto plates for use in the aforementioned drug screening techniques. Alternatively, non-neutralizing antibodies can be used to capture the peptide and immobilize it on a solid support. This invention also contemplates the use of competitive drug screening assays in which neutralizing antibodies capable of binding neuropilin-1 or/and VEGFR-2 specifically compete with a test compound for binding neuropilin-1 or/and VEGFR-2. In this manner, the antibodies can be used to detect the presence of any protein, which shares one or more antigenic determinants with neuropilin-1 and VEGFR-2

No genetic mutations of the VEGF gene, resulting in gene disruption, have thus far been linked to human disease, likely because absence of even a single VEGF allele is embryonically lethal[1,2,26]. Recently, however, impaired hypoxic regulation of VEGF has been shown to constitute a risk factor for ischemic heart disease[27] Whether this abnormal VEGF gene regulation—not function—may predispose to pathological disorders is, however, not known. In another embodiment of the invention polymorphisms in the regulatory region of the VEGF gene, which have an influence on the hypoxic regulation of said gene, can be detected and used diagnostically to identify patients at risk to develop a neuropathy or more specifically a motor neuropathy when exposed to brief periods of ischemia. Hypoxia-induced transcription of VEGF mRNA is mediated, at least in part, by the binding of hypoxia-inducible factor 1 (HIF-1) to an HIF-1 binding site located in the VEGF promotor. By the detection of polymorphisms that influence the hypoxic regulation of the VEGF gene it is also meant polymorphisms in the HIF-1 transcription factor, additional HIF-1-like factors, upstream regulators of HIF-1 and HIF-1-like transcription factors comprising the oxygen-sensor, additional factors binding to the 5' and 3' untranslated region of the VEGF mRNA and in the internal ribosomal entry site present in the 5' untranslated region of VEGF (Neufeld G. et al. FASEB J. 13, 9-22, 1999).

Several procedures have been developed for scanning genes in order to detect polymorphisms in genes. In terms of current use, many of the methods to scan or screen genes employ slab or capillary gel electrophoresis for the separation and detection step in the assays. Some of these methods comprise Single strand conformational polymorphism (SSCP) (Orita et al., "Detection of Polymorphisms of Human DNA by Gel Electrophoresis as Single-Stranded Conformation Polymorphisms," Proc. Natl. Acad. Sci. USA 86, 2766 (1989)), denaturing gradient gel electrophoresis (DGGE) (Abrams et al., "Comprehensive Detection of Single Base Changes in Human Genomic DNA Using Denaturing Gradient Gel Electrophoresis and a GC Clamp," Genomics 7, 463 (1990)), chemical cleavage at mismatch (CCM) (J. A. Saleeba & R. G. H. Cotton, "Chemical Cleavage of Mismatch to Detect Mutations," Methods in Enzymology 217, 286 (1993)), enzymatic mismatch cleavage (EMC) (R. Youil et al., "Screening for Mutations by Enzyme Mismatch Cleavage with T4 Endonuclease VII," Proc. Natl. Acad. Sci. USA 92, 87 (1995)), and "cleavase" fragment length polymorphism (CFLP). Still other methods focus on the use of mass spectrometry as a genetic analysis tool. Mass spectrometry requires minute samples, provides extremely detailed information about the molecules being analyzed including high mass accuracy, and is easily automated. U.S. Pat. No. 5,965,363 describes nucleic acid analysis by means of mass spectrometric analysis.

In another embodiment of the invention the Hypoxia Response Element (HRE) can be used for the treatment of neuron disorders or more specifically motor neuron disorders. VEGF, or homologous, derivates or fragments thereof, can be placed under hypoxic control by splicing said genes to one or more HRE elements. These constructs can then be used in gene therapy.

Gene therapy means the treatment by the delivery of therapeutic nucleic acids to patient's cells. This is extensively reviewed in Lever and Goodfellow 1995; Br. Med Bull., 51, 1-242; Culver 1995; Ledley, F. D. 1995. Hum. Gene Ther. 6, 1129. To achieve gene therapy there must be a method of delivering genes to the patient's cells and additional methods to ensure the effective production of any therapeutic genes. There are two general approaches to achieve gene delivery; these are non-viral delivery and virus-mediated gene delivery. The best characterized virus-mediated gene delivery system uses replication defective retroviruses to stably introduce genes into patients' cells.

The present invention will now be illustrated by reference to the following examples which set forth particularly advantageous embodiments. However, it should be noted that these embodiments are illustrative and cannot be construed as to restrict the invention in any way.

EXAMPLES

1. Targeted Deletion of the HIF-binding Site in the VEGF Promotor

Targeted deletion in the VEGF promotor of the hypoxia-response element (HRE), i.e. the binding site for the hypoxia-inducible factors (HIF) [23], was achieved using Cre/loxP-mediated targeting (FIG. 1), and confirmed by Southern blot analysis. Impaired hypoxic induction of VEGF in embryonic stem cells, homozygous for the HRE-deletion (VEGF$^{m/m}$), was confirmed by Northern blot analysis and by measurements of VEGF release during 36 h hypoxia (19±5 pg/ml after normoxia versus 45±6 pg/ml after hypoxia in VEGF$^{+/+}$ cells, n=6, p<0.05; 11±2 pg/ml after normoxia versus 13±3 pg/ml after hypoxia in VEGF$^{m/m}$ cells, n=6; p=NS). Deletion of the HIF-binding site in the VEGF gene was as effective as deletion of the HIF-1α gene itself [28] in abolishing hypoxic upregulation of VEGF (13±4 pg/ml after normoxia versus 14±2 pg/ml after hypoxia in HIF-1α$^{-/-}$ cells; n=6; p=NS). VEGF$^{m/m}$ embryos were recovered at a normal Mendelian frequency. Of the VEGF$^{m/m}$ mice, 30% died before birth and another 30% within the first postnatal days, while the remaining 40% survived more than 12 months. Here, the phenotype of the surviving VEGF$^{m/m}$ mice is described; the embryonic and neonatal phenotypes will be reported separately.

2. Motor Coordination and Muscular Performance in VEGF$^{m/m}$ Mice

VEGF$^{m/m}$ mice appeared normal until 4 months, but thereafter developed symptoms of motor neuron disease. They became progressively less mobile, and exhibited signs of severe muscle weakness and limb paresis. Beyond six months of age, mutant mice were too weak to turn over when placed on their back, slapped their feet while walking and had a waddling gait and scoliosis. When lifted by their tails, they reflexively contracted their limbs to the trunk and remained immobile, whereas wild type mice extended their limbs and struggled. VEGF$^{m/m}$ mice developed a coarse fur suggestive of impaired grooming and appeared thin along their flanks and legs. Notably, when asymptomatic two months old VEGF$^{m/m}$ mice were kept in a hypoxic chamber (10% $O_2$), they developed neurological signs (difficulty in turning over, reflex contracture when lifted by tail) within two weeks, indicating that hypoxia markedly accelerated the onset and progression of the phenotype. Beyond. 4 to 6 months of age, VEGF$^{m/m}$ mice performed significantly less well than wild type littermates in a number of motor coordination and muscle performance tests[29], including the treadmill-wheel test, grid test, rotating axle test and the footprint test (distance between the central pads of the hindfeet: 65±5 mm for VEGF$^{+/+}$ mice versus 45±5 mm for VEGF$^{m/m}$ mice; n=7; p<0.05). Compared to VEGF$^{+/+}$ mice, VEGF$^{m/m}$ mice were significantly less active at night (number of treadmill-wheel turns: 5400±600 for VEGF$^{+/+}$ mice versus 2700±400 for VEGF$^{m/m}$ mice; n=7; p<0.05) and for much shorter periods (minutes of intense activity: 150±40 for VEGF$^{+/+}$ mice versus 14±6 for VEGF$^{m/m}$; n=7; p<0.05). In the 'grid' test (mice are placed on a grid, that is subsequently turned upside-down), five of seven VEGF$^{+/+}$ mice hung on to the grid for at least one minute. Two VEGF$^{+/+}$ mice moved so actively that they dropped from the rack after 23 and 45 seconds. In contrast, four of six 20 week-old VEGF$^{m/m}$ mice fell already off the grid after 8 seconds, and only two mutant mice managed to hold on to the grid by not moving at all. When testing their grip strength (mice are forced to hang with their forelimbs on a horizontal thread), all VEGF$^{+/+}$ mice (n=7) immediately grabbed the thread with their hindlimbs. In contrast, VEGF$^{m/m}$ mice had difficulties in grabbing the thread with their hindlimbs, hung immobile and sagged. When they finally succeeded (five of six mice), VEGF$^{m/m}$ mice could not hold on to the thread and fell off. VEGF$^{m/m}$ mice also performed worse in the 'rotating axle' test, used to evaluate how long mice could stay on a rotating axle before falling off: all but one VEGF$^{+/+}$ mice (n=8) stayed on the axle for at least two minutes (time of analysis), whereas all of six VEGF$^{m/m}$ mice fell off after less than a minute (53±20 sec). Pain threshold, a sensory function measured as the paw-lick response in a hot plate test [29] was normal in VEGF$^{m/m}$ mice (the time to lick the front or rear paws for both genotypes was 7±1 s and 10±2 s, respectively; n=6; p=NS). However, VEGF$^{+/+}$ mice jumped out of the box after 100±20 s, whereas VEGF$^{m/m}$ mice were too weak to escape during this period.

3. Muscle Atrophy in VEGF$^{m/m}$ Mice

Skeletal muscles in VEGF$^{m/m}$ mice beyond 4 months of age showed signs of neurogenic atrophy. The wet weight of the plantar and dorsal flexor muscles was 170±14 mg and 92±19 mg in VEGF$^{+/+}$ mice versus 94±5 mg and 58±18 mg in VEGF$^{m/m}$ mice (n=3; p<0.05). Initially, a variable number of fibers were atrophic, but in older animals, most muscle fibers were severely atrophic, "angulated" or "elongated", characteristics of denervated fibers. Muscle fiber size was decreased by more than 50% in VEGF$^{m/m}$ mice (cross-sectional area: 1700±200 μm$^2$ in VEGF$^{+/+}$ mice versus 700±100 μm$^2$ in VEGF$^{m/m}$ mice; n=8; p<0.05). Regenerating muscle fibers, identified by their centrally located vesicular nucleus, smaller size and desmin-immunoreactivity, were commonly observed in VEGF$^{m/m}$ mice. Myosin ATPase staining revealed atrophy of all fiber types (type-I, -IIa, and -IIb). In contrast to the typical chessboard pattern of all fiber types in VEGF$^{+/+}$ mice, grouping of fibers of a similar type, a sign of reinnervation, was observed in VEGF$^{m/m}$ mice. Muscle spindles—involved in reflex control—were present in both genotypes (number of spindles/quadriceps section: 3.9±0.9 in VEGF$^{+/+}$ mice versus 4.5±0.8 in VEGF$^{m/m}$ mice; n=5; p=NS). Myopathic changes (sarcolemma desintegration, fiber necrosis, loss of muscle fibers, elevated plasma creatine kinase levels or fibrosis) were not detected in VEGF$^{m/m}$ mice. The muscle atrophy in VEGF$^{m/m}$ mice did not resemble the degenerative features of primary myopathies. Indeed, there was no loss of muscle fibers and, because of shrinkage, the density of the muscle fibers was increased in VEGF$^{m/m}$ mice (1250±190 cells/mm$^2$) as compared to VEGF$^{+/+}$ mice (720±80 cells/mm$^2$; p<0.05). Unlike in myopathies, there were no signs of fiber necrosis, sarcomere lysis or sarcolemma disruption (ultrastructural analysis; normal titin and desmin staining; absence of intracellular albumin), fatty infiltration, fibrosis (sirius red staining), or dystrophic calcification. Plasma levels of creatine kinase (released upon myocyte death) were normal in 8 month-old VEGF$^{m/m}$ mice (88±20 U/ml in VEGF$^{+/+}$ mice versus 94±9 U/ml in VEGF$^{m/m}$ mice; n=5; p=NS). In addition, atrophy was confined to skeletal and not to cardiac muscle, and was not caused by systemic disorders. Atrophy was confined to skeletal muscle fibers, since cardiomyocytes were not affected (cross-sectional area: 130±10 μm$^2$ in VEGF$^{+/+}$ mice versus 125±8 μm$^2$ in VEGF$^{m/m}$ mice; n=5; p=NS). Structural changes in muscle fibers were also not due to infectious disease (pathogen-free health report), inflammatory disorders of connective tissue or blood vessels (no signs of vasculitis), metabolic disorders (normal plasma glucose levels), or storage abnormalities in glycogen or lipids.

4. Motor Neuron Degeneration in VEGF$^{m/m}$ Mice

Evidence for a neurodegenerative process was obtained by analysis of the spinal cord and peripheral nerves. Nissl staining revealed a comparable number of neurons in the ventral horn in the spinal cord at young age (12 weeks) in both genotypes (neurons with a clearly identifiable cytoplasm/ventral horn section: 110±2 in VEGF$^{+/+}$ mice versus 107±6 in VEGF$^{m/m}$ mice; n=3; p=NS), indicating that deletion of the HIF-binding site in the VEGF promotor per se did not cause abnormal neuronal development. However, beyond 7 months of age, fewer neurons were detected in the ventral horn in VEGF$^{m/m}$ mice (neurons/ventral horn section: 110±3 in VEGF$^{+/+}$ mice versus 98±4 in VEGF$^{m/m}$ mice; n=8; p<0.05). Immunostaining for choline acetyltransferase (ChAT), a marker of motor neurons, revealed 30% fewer motor neurons in VEGF$^{m/m}$ than in VEGF$^{+/+}$ mice (ChAT-positive neurons/spinal cord section: 26±2 in VEGF$^{+/+}$ mice versus 18±2 in VEGF$^{m/m}$ mice; n=4; p=0.05). In contrast to VEGF$^{+/+}$ mice, the neuronal cell bodies (perikarya) and proximal axons of motor neurons in VEGF$^{m/m}$ mice contained inclusions of phosphorylated neurofilament (NF$_P$), a hallmark of motor neuron disease[31] (number of NF$_P$-positive neurons/spinal cord section: none in VEGF$^{+/+}$ mice versus 7±2 in VEGF$^{m/m}$ mice; n=6; p<0.05). These NF$_P$-positive motor neurons were smaller in size (250±20 μm$^2$) than NF$_P$-negative motor neurons in VEGF$^{+/+}$ mice (500±40 μm$^2$; n=4, p<0.05). The complexity and occurrence of dephosphorylated neurofilament (NF)-positive axons and of MAP-2-positive dendrites was comparable in both genotypes, even though more neurons in VEGF$^{m/m}$ mice tended to accumulate dephosphorylated NF in their perikaryon. Focal axon swellings ('spheroids'), also found in ALS patients[33,34], occurred in the spinal cord in VEGF$^{m/m}$ but not in VEGF$^{+/+}$ mice (number of swollen axons/spinal cord section at 31 weeks of age: none in VEGF$^{+/+}$ mice versus 17±1 in VEGF$^{m/m}$ mice; n=7). Swollen axons with dense axoplasm were primarily located in the ventral horn, whereas the dorsal spinal cord or the corticospinal tracts appeared relatively spared. A fraction of these swollen axons was immunoreactive for synaptophysin, a sign of impaired axonal transport, and for ubiquitin, which binds damaged proteins in neurodegenerative conditions such as ALS[35]. They often contained neurofilament inclusions, as revealed by Bielschowski staining and immunostaining for phosphorylated neurofilament (NF$_P$). Compared to VEGF$^{+/+}$ mice, a prominent reactive astrocytosis was consistently observed in the spinal cord of VEGF$^{m/m}$ mice, but characteristically only in the ventral horn. Numerous hypertrophic astrocytes accumulated in the ventral and intermediate zones (GFAP-positive area in gray matter: 0.8±0.4% in VEGF$^{+/+}$ mice versus 7±1% in VEGF$^{m/m}$ mice; n=4; p<0.05), and in the ventral white matter (GFAP-positive area in white matter: 8±3% in VEGF$^{+/+}$ mice versus 31±2% in VEGF$^{m/m}$ mice; n=4; p<0.05).

5. Axon Degeneration in VEGF$^{m/m}$ Mice

Signs of Wallerian degeneration and significant loss of large axons were found. Some fibers were completely replaced by the more numerous activated macrophages, phagocytosing disrupted myelin sheets (number of F4/80-positive cells/mm$^2$: 150±27 in VEGF+/+ mice versus 340±20 in VEGF$^{m/m}$ mice; n=6; p<0.05). Endoneural fibrosis and expression of GFAP, a marker of denervated Schwann cells, were more prominent in mutant nerves.

6. Electrophysiology of VEGF$^{m/m}$ Mice

Electromyographic (EMG) recordings during rest and muscle contraction revealed clear signs of denervation and reinnervation. Diffuse spontaneous activity (fibrillation potentials, isolated or salvo's of positive sharp waves), together with polyphasic motor unit action potentials (MUAP's) of normal amplitude, and unstable satellite potentials were observed in the superficial gastrocnemius muscle, the paravertebral muscles and the diaphragm in VEGF$^{m/m}$ but not in VEGF$^{+/+}$ mice. In the diaphragm, denervation was evidenced by a reduced recruitment of MUAP's during inspiration in VEGF$^{m/m}$ mice (number of MUAP's per inspiratory burst: 124±20 in VEGF$^{+/+}$ mice versus 56±4 in VEGF$^{m/m}$ mice; n=7; p<0.05). Compared to the normal bi- or triphasic pattern of MUAPs in VEGF$^{+/+}$ mice, long-duration polyphasic MUAP's were regularly detected. The duration of inspiratory bursts in VEGF$^{m/m}$ mice remained normal (2300±230 ms in VEGF$^{+/+}$ mice versus 2100±300 ms in VEGF$^{m/m}$ mice; n=7; p=NS), and the amplitude of the largest diaphragmatic MUAP's were preserved in VEGF$^{m/m}$ mice (MUAPs with an amplitude >200 μV per inspiratory burst: 14±2 in VEGF$^{+/+}$ mice versus 11±4 in VEGF$^{m/m}$ mice, n=7; p=NS), consistent with an ongoing process of denervation and reinnervation. Furthermore, in contrast to the innervation of individual endplates by a single terminal axon, terminal axons in VEGF$^{m/m}$ mice more often branched as thin (presumably unmyelinated) sprouts to two or more endplates. Latencies of compound muscle action potentials (measured from site of stimulation to site of recording) were somewhat increased in mutant mice (810±36 μs in VEGF$^{+/+}$ mice versus 1030±44 μs in VEGF$^{m/m}$ mice; n=7; p<0.05), compatible with the axonal loss. Sensory nerve function appeared electrophysiologically normal: sensory nerve action potential (SNAP) amplitudes were 100±7 μV in VEGF$^{m/m}$ mice versus 120±14 μV in VEGF$^{m/m}$ mice (n=5; p=NS), and sensory nerve conduction velocities were 33±2 m/s in VEGF$^{+/+}$ mice versus 30±2 m/s in VEGF$^{m/m}$ mice (n=5; p=NS). These findings are consistent with a purely motor neurogenic disorder.

7. Normal Vascular Growth in VEGF$^{m/m}$ Mice

Because of the well-known angiogenic role of VEGF, VEGF$^{m/m}$ mice were examined for vascular defects. However, there were no signs of vascular insufficiency in the skeletal muscle, peripheral nerves, or spinal cord. (i) In muscle, because of the atrophy, capillary densities were higher in VEGF$^{m/m}$ than in VEGF$^{+/+}$ mice (capillaries/mm$^2$: 1200±150 in VEGF$^{+/+}$ mice versus 1740±150 in VEGF$^{m/m}$ mice; n=5; p<0.05). Fluoro-angiography[6] of the diaphragm revealed comparable vascularization in both genotypes. (ii) Sciatic nerves in VEGF$^{m/m}$ mice had a similar density of vasa nervorum (capillaries/mm$^2$: 90±6 in VEGF$^{+/+}$ mice versus 100±7 in VEGF$^{m/m}$ mice; n=7; p=NS), were normally perfused (laser doppler blood flow perfusion units: 150±15 in VEGF$^{+/+}$ mice versus 190±12 in VEGF$^{m/m}$ mice; n=5; p=NS), and contained a comparable density and pattern of peri- and endoneural vessels without signs of leakiness or obstruction (fluoro-angiography). Axonal degeneration occurred in the periphery as well as in the center of VEGF$^{m/m}$ nerves, arguing against ischemic neuropathy, which is typically more severe in the center[37]. (iii) In the spinal cord, capillary densities were comparable in both genotypes in the gray matter (capillaries/mm$^2$: 380±17 in VEGF$^{+/+}$ mice versus 390±13 in VEGF$^{m/m}$ mice; n=7; p=NS), and in the white matter (capillaries/mm$^2$: 170±12 in VEGF$^{+/+}$ mice versus 170±11 in VEGF$^{m/m}$ mice; n=7; p=NS), with similar densities in ventral and dorsal horns. Endothelial cells of both genotypes expressed blood-brain barrier characteristics (glucose-transporter type I; Glut-1). Signs of ischemic or diabetic microangiopathy[38] were not detected in VEGF$^{m/m}$ mice. Characteristic signs of ischemic neuropathy (amyloid deposits, inflammatory vasculitis) or diabetic neuropathy (hyalinization of endoneural microvessels, thickening of capillary basement membrane, pericyte drop-out, lumen obstruction due to endothelial hyperplasia/hypertrophy, neovascularization, nerve infarct) were not deteced in VEGF$^{m/m}$ mice. The muscle weakness in VEGF$^{m/m}$ mice was not due to impaired oxygenation, nor to reduced levels of the $O_2$-carrier hemoglobin (normal hematological profile). In addition, echocardiographic determination of the circumferential fiber shortening ($VC_F$, a measure of contractility) revealed that VEGF$^{m/m}$ mice had normal cardiac function during baseline conditions (15+2 in VEGF$^{+/+}$ mice versus 17±3 in VEGF$^{m/m}$ mice; p=NS) and after dobutamine-stress (27±6 in VEGF$^{+/+}$ mice versus 26±6 in VEGF$^{m/m}$ mice; p=NS). There was also no metabolic imbalance in mutant mice (normal electrolytes; plasma glucose levels: 200±10 mg/dl in VEGF$^{+/+}$ mice versus 180±16 in VEGF$^{m/m}$ mice, n=7; p=NS).

After exposure to hypoxia (10% $O_2$; 24 h), motor neurons in both genotypes stained comparably for the hypoxia-marker pimonidazole. The muscle weakness in VEGF$^{m/m}$ mice was not due to impaired oxygenation, anemia, metabolic imbalance, cardiac dysfunction, or abnormal vascular development in other organs. Collectively, there were no signs of vascular insufficiency or ischemia in VEGF$^{m/m}$ mice.

8. Expression of VEGF and Neuropilin-1 in the Spinal Cord

Exposure of VEGF$^{+/+}$ mice to hypoxia (10% $O_2$; 24 h) upregulated expression of VEGF in the spinal cord (pg/mg protein: 15±1 in normoxia versus 94±20 in hypoxia; n=7, p<0.05), but only minimally in VEGF$^{m/m}$ mice (pg/mg protein: 9±2 in normoxia versus 15±2 in hypoxia; n=7; p=0.06). Hypoxic induction of LDH-A (another hypoxia-inducible gene) in VEGF$^{m/m}$ spinal cords was not abrogated (LDH-A/$10^3$ hprt mRNA copies: 230±100 during normoxia versus 1100±400 during hypoxia; n=7; p<0.05), confirming specificity of gene targeting. Similar results were obtained in the brain. In contrast, VEGF levels were reduced in skeletal muscle after hypoxia (pg/mg protein: 40±10 in normoxia and 22±9 in hypoxia in VEGF$^{+/+}$ mice, n=7, p<0.05 versus 52±6 in normoxia and 23+4 in hypoxia in VEGF$^{m/m}$ mice, n=7; p<0.05), consistent with previous observations that VEGF expression in response to hypoxia is tissue-specific[39].

9. Neurotrophic Role of VEGF and Neuropilin-1

Apoptosis of neuronal cells has been implicated in several neurodegenerative disorders, including ALS[24,33]. A possible neuroprotective role of VEGF, independently of its angiogenic effect, was studied using NSC34 cells, a murine motor neuron cell line[40], in response to various apoptotic stimuli. Known motor neuron survival factors (bFGF[41], TGFβ-1[42]) protected NSC34 cells against TNF-α-induced apoptosis (FIG. 5a). Physiological concentrations of VEGF$_{165}$ also protected motor neurons against apoptosis induced by TNF-α, hypoxia, oxidative stress ($H_2O_2$), and serum deprivation. Notably, VEGF$_{121}$ (which does not bind NP-1[10]) did not rescue motor neurons. Involvement of NP-1 was demonstrated by the partial neutralization of the VEGF$_{165}$ survival effect by antibodies, blocking NP-1 but not by antibodies blocking NP-2. The neurotrophic effect of VEGF$_{165}$ was also partially blocked by antibodies to VEGFR-2 but not to VEGFR-1, while complete neutralization was achieved by the combination of both VEGR-2 and NP-1 antibodies. NP-1 is known to bind semaphorin III/collapsin-1 (Sema3A), implicated in repulsion and patterning of sensory and motor projections in the spinal cord during development[11-15] Sema3A was recently suggested to promote apoptosis of sympathetic and cerebellar neurons[43], and to prevent axonal regeneration after nerve injury in the adult[44] (and, therefore, could be implicated in axon retraction and motor neuron death in VEGF$^{m/m}$ mice), Exposure of wild type mice to hypoxia (10% $O_2$; 24 h) slightly increased expression of Sema3A in the spinal cord. SCN34 motor neurons also expressed Sema3A. Thus, motor neurons express both a neuroprotective factor (VEGF$_{165}$) as well as a neurorepulsive/apoptotic factor (Sema3A), that are reciprocal antagonists for binding to NP-1.

10. Abnormal Neuronal Perfusion in VEGF$^{m/m}$ Mice

We examined whether the muscle weakness and neuropathy were caused by vascular insufficiency. In VEGF$^{m/m}$ skeletal muscle, only a reduction in capillary lumen size could be detected, but microvascular partial oxygen pressure measurements revealed that the smaller capillaries did not cause muscle ischemia. Importantly, the capillary-to-muscle ratio was normal when the first signs of neurogenic muscle atrophy developed, showing that impaired angiogenesis was not the cause of motor neuron degeneration. Instead, the slight decrease of this ratio in old VEGF$^{m/m}$ mice with severe muscle atrophy beyond 7 months may be the result of muscle denervation, as observed in patients with denervation muscle atrophy (Carpenter et al. (1982) *Muscle Nerve* 5, 250). Furthermore, PCNA-labeling failed to detect genotypic differences in endothelial proliferation in skeletal muscle at all ages and fluoro-angiography (Schratzberger P. et al. (2000) *Nat Med* 6, 405) of the diaphragm revealed comparable vascularization in both genotypes. No obvious structural vascular defects could be detected in neuronal tissue but, surprisingly, neuronal perfusion was reduced by 50% in VEGF$^{m/m}$ mice. In sciatic nerves, both genotypes had a comparable density of vasa nervorum (capillaries/mm$^2$: 90±6 in VEGF$^{+/+}$ mice versus 100±7 in VEGF$^{m/m}$ mice; n=7; p=NS) and pattern of peri- and endoneural vessels without signs of leakiness or obstruction (fluoro-angiography). In the spinal cord, capillary densities were comparable in both genotypes in the gray matter (capillaries/mm$^2$: 380±17 in VEGF$^{+/+}$ mice versus 390±13 in VEGF$^{m/m}$ mice; n=7; p=NS) and in the white matter (capillaries/mm$^2$: 170±12 in VEGF$^{+/+}$ mice versus 170±11 in VEGF$^{m/m}$ mice; n=7; p=NS), with similar densities in ventral and dorsal horns. Endothelial cells in VEGF$^{m/m}$ mice expressed blood-brain barrier characteristics (glucoseransporter type I; Glut-1), but ultrastructural signs of diabetic microangiopathy (Boulton A. J. et al. (1998) *Med Clin North Am* 82, 909) were not detected. Because of the inaccessibility and small size of the spinal cord, blood flow was quantified in the brain using microspheres. Baseline cerebral blood flow was 0.9±0.1 ml/min/g in VEGF$^{+/+}$ mice versus 0.5±0.1 in VEGF$^{m/m}$ mice (n=8; p<0.05). VEGF$^{m/m}$ mice were, however, still able to increase their cerebral blood flow in reponse to hypercapnia (7.5% $CO_2$), as measured using laser doppler (% increase of flow: 43±3% in $VEGF^{+/+}$ mice versus 39±6% in $VEGF^{m/m}$ mice; n=10; p=NS). The neuronal perfusion deficit appeared to be specific as renal perfusion was normal in $VEGF^{m/m}$ mice (1.5±0.2 ml/min/g in $VEGF^{+/+}$ mice versus 1.8±0.3 in $VEGF^{m/m}$ mice; n=8; p=NS). It should be clear that characteristic signs of diabetic neuropathy (hyalinization of endoneural microvessels, thickening of capillary basement membrane, pericyte drop-out, lumen obstruction due to endothelial hyperplasia/hypertrophy, neovascularization, nerve infarct) were not detected in $VEGF^{m/m}$ mice. Furthermore, the muscle weakness in $VEGF^{m/m}$ mice was not due to impaired oxygenation, nor to reduced levels of the $O_2$-carrier hemoglobin (normal hematological profile). In addition, echocardiographic determination of the circumferential fiber shortening ($VC_F$, a measure of contractility) revealed that $VEGF^{m/m}$ mice had normal cardiac function during baseline conditions (15±2 in $VEGF^{+/+}$ mice versus 17±3 in $VEGF^{m/m}$ mice; p=NS) and after dobutamine-stress (27±6 in $VEGF^{+/+}$ mice versus 26±6 in $VEGF^{m/m}$ mice; p=NS). There was also no metabolic imbalance in mutant mice (normal electrolytes; plasma glucose levels: 200±10 mg/dl in $VEGF^{+/+}$ mice versus 180±16 in $VEGF^{m/m}$ mice, n=7; p=NS). In conclusion, the muscle weakness and neuropathy in $VEGF^{m/m}$ mice were not due to reduced oxygen saturation levels in the blood, anemia, metabolic imbalance or cardiac dysfunction.

Materials and Methods

1. Generation of $VEGF^{m/m}$ Mice

The murine VEGF gene (129/SvJ; Genome Systems Inc., St. Louis, Mo.) was isolated and mapped previously[26]. Deletion of the HIF-1alfa binding site in the VEGF promoter was achieved by constructing a targeting vector, pBSK.VEGF$^m$, in which the wild type TACGTGGG HIF-1alfa response element (HRE) was deleted, which abolishes HIF-1alfa binding[23]. This vector contained a neomycin phosphotransferase (neo) cassette, flanked by loxP sites to allow subsequent removal by Cre-recombinase (FIG. 1a). After electroporation of pBSK.VEGF$^m$, recombined ES cell clones, containing both the HIF-1alfa binding site deletion and the floxed neo-cassette ($VEGF^{+/neo}$) were identified by Southern blot analysis and sequencing (FIG. 1a). $VEGF^{neo/neo}$ ES cells were obtained by culturing $VEGF^{+/neo}$ ES cells in high G418 selection (1800 µg/ml), and used to obtain $VEGF^{m/m}$ ES cells by transient expression of the Cre recombinase. Probes for Southern blot analysis included: probe A (0.7 kb PstI/BstEII fragment) and probe B (1 kb PCR fragment, amplified from genomic DNA, using as forward primer 5'-TTA TCA GM TTC ATT CCC GAG GCC TGG GGA GAG TTG GG-3' and as reverse primer 5'-ATA MG AAT TCG GAA GGT CAC AGC CCT TCG GTG G-3'). Analytical restriction digests used for identification of recombinant ES cell clones are indicated. Targeted $VEGF^{+/neo}$ ES clones were used to generate chimeric mice via morula aggregation, that were testbred with Swiss females for germline transmission. Viable $VEGF^{+/neo}$ offspring were not obtained, presumably because the presence of the neo-gene inactivated VEGF gene expression and caused haploinsufficient lethality. However, when chimeric mice were intercrossed with pgk:Cre mice, viable $VEGF^{+/m}$ offspring were obtained, that were intercrossed to obtain homozygous $VEGF^{m/m}$ offspring. All methods of ES culture, selection, and diploid aggregation have been described[26].

2. Gene Expression, Morphology, Motor Performance Tests, Torque and Electromyography Western and Northern blotting, quantitative real-time RT-PCR, histology, electron microscopy, immunostaining, alone or in combination with in situ hybridization, and morphometric analysis were performed as previously described[4,26,56]. The following antibodies were used for immunostaining: Glut-1 (C-20; Santa Cruz Biotechnology Inc, Santa Cruz, Calif.), VEGF (Santa Cruz), desmin (D33; Dako S/A, Glostrup, Denmark), ChAT (AB144; Chemicon, Biognost, Wevelgem), NF (SM32; Sternberger Monoclonals Inc., Lutherville, Md.), $NF_P$ (SMI 31; Sternberger Monoclonals Inc.), calretinin (Swant, Bellinzon, Switzerland), MAP2 (Sigma, Bornem, Belgium), GFAP (Z0334; Dako S/A), ubiquitin (Z0458; Dako S/A), synaptophysin (A0010; Dako S/A), F4/80 (A3-1; Serotec Ltd, Oxford, UK), pimonidazole hydrochloride (Hypoxyprobe-1; Natural Pharmacia International Inc., Belmont, Md.), BrdU (Beckton Dickinson, Brussels, Belgium). Histochemical staining (myosin ATPase, Nissl, Bielschowsky) was performed using standard protocols. All stainings were performed on 7 µpm-thick sections, except for ChAT (40 µm), Nissl (15 µm) and myosine ATPase (15 µm). Quantitative real-time RT-PCR analysis was performed as previously described[56]. The relative expression levels of these genes were calculated by dividing their signals by the signals obtained for the HPRT gene.

Motor coordination and muscular performance tests (footprint test, hanging test, grip test, rotating axle test)[29], electromyographic recordings in anesthetized mice[58], and echocardiographic analysis[56] were performed as described. All animal procedures were approved by the ethical committee. For fluoro-angiography[6], 500 µl of 5% fluorescent dextran (molecular weight of 2×10$^6$ dalton; Sigma) was injected intravenously in urethane-anesthetized mice. After 5 minutes, mice were perfused with 1.9 ml fluorescent dextran and 100 µl adenocor (Sanofi Pharma, Brussels, Belgium), and sciatic nerves were immediately analyzed by confocal microscopy. Laser-doppler measurements of blood flow (blood perfusion units) through sciatic nerves was performed in anesthetized mice using a needle flow probe (ADInstruments Pty Ltd, Castle Hill, Australia) at 1 mm intervals across a 5 mm nerve segment. Analysis of blood gases, clinical chemistry and hematologic profile was performed using standard techniques at the University Hospital (Leuven, Belgium).

3. Cell Culture and Survival Analysis

SCN-34 cells were cultured as described[40]. Blocking antibodies to NP-1 and NP-2 were a gift from Dr. A. Kolodkin, and VEGFR-2 antibodies (DC101) from Dr. P. Bohlen, (Imclone). For apoptosis studies, SCN-34 cells were cultured in T75 flasks coated with 0.1% gelatin in RPMI 1640 medium containing 10% foetal calf serum (Life Technologies, Paisley, UK), 100 IU/ml penicillin, 100 µg/ml streptomycin, 2 mM glutamine, heparin (100 µg/ml) and endothelial cell growth supplement (30 µg/ml). Apoptosis was induced by supplementation of TNF-alfa (50 ng/ml; R&D, Abingdon, UK), withdrawal of growth factors (0.1% or 0.5% fetal calf serum), or treatment with hypoxia (2% $O_2$) or 2% $H_2O_2$. $VEGF_{121}$ and $VEGF_{165}$ were from R&D. Apoptosis was quantified by measuring cytoplasmic histone-associated DNA fragments (mono- and oligonucleosomes) using a photometric enzyme immunoassay (Cell Detection ELISA, Boehringer Mannheim, Mannheim, Germany). Determination of VEGF levels was performed using commercially available ELISAs (R&D).

REFERENCES

1. Carmeliet, P. Mechanisms of angiogenesis and arteriogenesis. *Nat Med* 6, 389-395 (2000).
2. Ferrara, N. & Alitalo, K. Clinical applications of angiogenic growth factors and their inhibitors. *Nat Med* 5, 1359-1364 (1999).
3. van Bruggen, N. et al. VEGF antagonism reduces edema formation and tissue damage after ischemia/reperfusion injury in the mouse brain. *J Clin Invest* 104, 1613-1620 (1999).
4. Plate, K. H., Beck, H., Danner, S., Allegrini, P. R. & Wiessner, C. Cell type specific upregulation of vascular endothelial growth factor in an MCA-occlusion model of cerebral infarct. *J Neuropathol Exp Neurol* 58, 654-666 (1999).
5. Hayashi, T. et al. Expression of angiogenic factors in rabbit spinal cord after transient ischaemia. *Neuropathol Appl Neurobiol* 25, 63-71 (1999).
6. Schratzberger, P. et al. Favorable effect of VEGF gene transfer on ischemic peripheral neuropathy. *Nat Med* 6, 405-413 (2000).
7. Sondell, M., Lundborg, G. & Kanje, M. Vascular endothelial growth factor has neurotrophic activity and stimulates axonal outgrowth, enhancing cell survival and Schwann cell proliferation in the peripheral nervous system. *J Neurosci* 19, 5731-5740 (1999).
8. Sondell, M., Lundborg, G. & Kanje, M. Vascular endothelial growth factor stimulates schwann cell invasion and neovascularization of acellular nerve grafts. *Brain Res* 846, 219-228 (1999).
9. Miao, H. Q. et al. Neuropilin-1 mediates collapsin-1/semaphorin III inhibition of endothelial cell motility: functional competition of collapsin-1 and vascular endothelial growth factor-165. *J Cell Biol* 146, 233-242 (1999).
10. Soker, S., Takashima, S., Miao, H. Q., Neufeld, G. & Klagsbrun, M. Neuropilin-1 is expressed by endothelial, and tumor cells as an isoform-specific receptor for vascular endothelial growth factor. *Cell* 92, 735-745 (1998).
11. Fujisawa, H. & Kitsukawa, T. Receptors for collapsin/semaphorins. *Curr Opin Neurobiol* 8, 587-592 (1998).
12. He, Z. & Tessier-Lavigne, M. Neuropilin is a receptor for the axonal chemorepellent Semaphorin III. *Cell* 90, 739-751 (1997).
13. Yu, H. H. & Kolodkin, A. L. Semaphorin signaling: a little less per-plexin. *Neuron* 22, 11-14 (1999).
14. Raper, J. A. Semaphorins and their receptors in vertebrates and invertebrates. *Curr Opin Neurobiol* 10, 88-94 (2000).
15. Varela-Echavarria, A., Tucker, A., Puschel, A. W. & Guthrie, S. Motor axon subpopulations respond differentially to the chemorepellents netrin-1 and semaphorin D. *Neuron* 18, 193-207 (1997).
16. Knight, J. A. Reactive oxygen species and the neurodegenerative disorders. *Ann Clin Lab Sci* 27, 11-25 (1997).
17. Bromberg, M. B. Pathogenesis of amyotrophic lateral sclerosis: a critical review. *Curr Opin Neurol* 12, 581-588 (1999).
18. Robberecht, W. L. & de Jong, J. M. B. V. Oxidative stress in amyotrophic lateral sclerosis: pathogenic mechanism or epiphenomenon? in *Amyotrophic Lateral Sclerosis*. (eds. Brown, R. H. J., Meininger, V. & Swash, M.) 211-222 (Martin Dunitz Ltd., London, 2000).
19. Green, S. L. & Tolwani, R. J. Animal models for motor neuron disease. *Lab Anim Sci* 49, 480-487 (1999).
20. Beal, M. F. et al. Increased 3-nitrotyrosine in both sporadic and familial amyotrophic lateral sclerosis [see comments]. *Ann Neurol* 42, 644-654 (1997).
21. Ferrante, R. J. et al. Evidence of increased oxidative damage in both sporadic and familial amyotrophic lateral sclerosis. *J Neurochem* 69, 2064-2074 (1997).
22. Dor, Y. & Keshet, E. Ischemia-driven angiogenesis. *Trends Cardiovasc Med* 7, 289-294 (1997).
23. Semenza, G. L. Expression of hypoxia-inducible factor 1: mechanisms and consequences. *Biochem Pharmacol* 59, 47-53 (2000).
24. Kilpatrick, T. J. & Soilu-Hanninen, M. Molecular mechanisms regulating motor neuron development and degeneration. *Mol Neurobiol* 19, 205-228 (1999).
25. Pettmann, B. & Henderson, C. E. Neuronal cell death. *Neuron* 20, 633-647 (1998).
26. Carmeliet, P. et al. Abnormal blood vessel development and lethality in embryos lacking a single vascular endothelial growth factor allele. *Nature* 380, 435-439 (1996).
27. Schultz, A. et al. Interindividual heterogeneity in the hypoxic regulation of VEGF: significance for the development of the coronary artery collateral circulation. *Circulation* 100, 547-552 (1999).
28. Carmeliet, P. et al. Role of HIF-1alpha in hypoxia-mediated apoptosis, cell proliferation and tumour angiogenesis. *Nature* 394, 485-490 (1998).
29. Tilson, H. A. & Mitchell, C. L. Neurobehavioral techniques to assess the effects of chemicals on the nervous system. *Annu Rev Pharmacol Toxicol* 24, 425-450 (1984).
30. Hamelmann, E. et al. Noninvasive measurement of airway responsiveness in allergic mice using barometric plethysmography. *Am J Respir Crit Care Med* 156, 766-775 (1997).
31. Lee, M. K. & Cleveland, D. W. Neuronal intermediate filaments. *Annu Rev Neurosci* 19, 187-217 (1996).
32. Dal Canto, M. C. & Gurney, M. E. Development of central nervous system pathology in a murine transgenic model of human amyotrophic lateral sclerosis. *Am J Pathol* 145, 1271-1279 (1994).
33. Martin, L. J., Price, A. C., Kaiser, A., Shaikh, A. Y. & Liu, Z. Mechanisms for neuronal degeneration in amyotrophic lateral sclerosis and in models of motor neuron death. *Int J Mol Med* 5, 3-13 (2000).
34. Bernstein, M. & Lichtman, J. W. Axonal atrophy: the retraction reaction. *Curr Opin Neurobiol* 9, 364-370 (1999).
35. Lowe, J., Mayer, R. J. & Landon, M. Ubiquitin in neurodegenerative diseases. *Brain Pathol* 3, 55-65 (1993).
36. Kawamura, Y., Okazaki, H., O'Brien, P. C. & Dych, P. J. Lumbar motoneurons of man: I) number and diameter histogram of alpha and gamma axons of ventral root. *J Neuropathol Exp Neurol* 36, 853-860 (1977).
37. Mackenzie, M. L. & Alit, G. The vasa nervorum: microcorrosion casts for scanning electron microscopy. *Acta Anat* 136, 319-324 (1989).
38. Boulton, A. J. & Malik, R. A. Diabetic neuropathy. *Med Clin North Am* 82, 909-929 (1998).
39. Marti, H. H. & Risau, W. Systemic hypoxia changes the organ-specific distribution of vascular endothelial growth factor and, its receptors. *Proc Natl Acad Sci USA* 95, 15809-15814 (1998).
40. Cashman, N. R. et al. Neuroblastoma x spinal cord (NSC) hybrid cell lines resemble developing motor neurons. *Dev Dyn* 194, 209-221 (1992).

41. Grothe, C. & Wewetzer, K. Fibroblast growth factor and its implications for developing and regenerating neurons. *Int J Dev Biol* 40, 403-410 (1996).
42. Iwasaki, Y., Shiojima, T., Tagaya, N., Kobayashi, T. & Kinoshita, M. Effect of transforming growth factor beta 1 on spinal motor neurons after axotomy. *J Neurol Sci* 147, 9-12 (1997).
43. Shirvan, A. et al. Semaphorins as mediators of neuronal apoptosis. *J Neurochem* 73, 961-971 (1999).
44. Pasterkamp, R. J., Giger, R. J. & Verhaagen, J. Regulation of semaphorin III/collapsin-1 gene expression during peripheral nerve regeneration. *Exp Neurol* 153, 313-327 (1998).
45. Gerber, H. P. et al. VEGF is required for growth and survival in neonatal mice. *Development* 126, 1149-1159 (1999).
46. Benjamin, L. E., Hemo, I. & Keshet, E. A plasticity window for blood vessel remodelling is defined by pericyte coverage of the preformed endothelial network and is regulated by PDGF-B and VEGF. *Development* 125, 1591-1598 (1998).
47. Dyck, P. J. & Giannini, C. Pathologic alterations in the diabetic neuropathies of humans: a review. *J Neuropathol Exp Neurol* 55, 1181-1193 (1996).
48. Nohl, H., Staniek, K. & Gille, L. Imbalance of oxygen activation and energy metabolism as a consequence or mediator of aging. *Exp Gerontol* 32, 485-500 (1997).
49. Copin, J. C. et al. Oxygen deprivation but not a combination of oxygen, glucose, and serum deprivation induces DNA degradation in mouse cortical neurons in vitro: attenuation by transgenic overexpression of CuZn-superoxide dismutase. *J Neurotrauma* 13, 233-244 (1996).
50. Ochiai-Kanai, R., Hasegawa, K., Takeuchi, Y., Yoshioka, H. & Sawada, T. Immunohistochemical nitrotyrosine distribution in neonatal rat cerebrocortical slices during and after hypoxia. *Brain Res* 847, 59-70 (1999).
51. Hellwig-Burgel, T., Rutkowski, K., Metzen, E., Fandrey, J. & Jelkmann, W. Interleukin-1beta and tumor necrosis factor-alpha stimulate DNA binding of hypoxia-inducible factor-1. *Blood* 94, 1561-1567 (1999).
52. Yun, J. K., McCormick, T. S., Judware, R. & Lapetina, E. G. Cellular adaptive responses to low oxygen tension: apoptosis and resistance. *Neurochem Res* 22, 517-521 (1997).
53. Lorez, H., Keller, F., Ruess, G. & Otten, U. Nerve growth factor increases in adult rat brain after hypoxic injury. *Neurosci Lett* 98, 339-344 (1989).
54. Klempt, N. D. et al. Hypoxia-ischemia induces transforming growth factor beta 1 mRNA in the infant rat brain. *Brain Res Mol Brain Res* 13, 93-101 (1992).
55. Takahashi, T. et al. Plexin-neuropilin-1 complexes form functional semaphorin-3A receptors. *Cell* 99, 59-69 (1999).
56. Carmeliet, P. et al. Impaired myocardial angiogenesis and ischemic cardiomyopathy in mice lacking the vascular endothelial growth factor isoforms VEGF164 and VEGF188. *Nat Med* 5, 495-502 (1999).
57. Gorselink, M. et al. Accurate measurements of in situ isometric contractile properties of hind limb plantar and dorsal flexor muscle complex of intact mice. *Eur. J. Physiol.* 439, 665-670 (2000).
58. Kennel, P. F. et al. Electromyographical and motor performance studies in the pmn mouse model of neurodegenerative disease. *Neurobiol Dis* 3, 137-147 (1996).
59. de Lima, A. D., Merten, M. D. & Voigt, T. Neuritic differentiation and synaptogenesis in serum-free neuronal cultures of the rat cerebral cortex. *J Comp Neurol* 382, 230-246 (1997).
60. de Hoop, M. J., Meyn, L. & Dotti, C. G. Culturing hippocampal neurons and astrocytes from fetal brain. Cell Biology: a laboratory handbook., Vol. 1 154-163 (Academic Press, 1998).

The invention claimed is:

1. A method of treating amyotrophic lateral sclerosis (ALS) in a mammal, the method consisting essentially of administering to the mammal a neuroprotective amount of a VEGF-A protein, wherein the VEGF-A protein is isoform VEGF$_{165}$ and wherein the VEGF-A protein is administered intrathecally.

2. The method of claim 1, wherein the administration is by infusion.

3. The method of claim 2, wherein the infusion is by an implanted pump.

4. The method of claim 3, wherein the intrathecal administration is by catheter to the spine.

5. A method of enhancing survival of a motor neuron in a mammal, the method consisting essentially of administering to the mammal an amount of a VEGF-A protein effective to enhance survival of the motor neuron, wherein the VEGF-A protein is isoform VEFG$_{165}$ and wherein the VEGF-A protein is administered intrathecally.

6. The method of claim 5, wherein the motor neuron is hypoxic.

7. The method of claim 5, wherein the administration is by infusion.

8. The method of claim 7, wherein the infusion is by an implanted pump.

9. The method of claim 8, wherein the intrathecal administration is by catheter to the spine.

10. A method of enhancing survival of a motor neuron, the method consisting essentially of contacting the motor neuron in vitro with an amount of a VEGF-A protein effective to enhance survival of the motor neuron, wherein the VEGF-A protein is isoform VEGF$_{165}$.

11. The method of claim 10, wherein the motor neuron is hypoxic, under oxidative stress, or under serum deprivation.

12. A method of treating amyotrophic lateral sclerosis (ALS) in a mammal, the method consisting essentially of administering to the mammal a neuroprotective amount of a VEGF-A protein in a manner effective to treat ALS in the mammal, wherein the VEGF-A protein is isoform VEGF$_{165}$.

13. The method of claim 12, wherein the VEGF-A protein is administered in a manner effective to bring the VEGF-A protein in contact with motor neurons in the central nervous system of the mammal.

14. A method of enhancing survival of a motor neuron in a mammal, the method consisting essentially of administering to the mammal an amount of a VEGF-A protein effective to enhance survival of the motor neuron, wherein the VEGF-A protein is isoform VEGF$_{165}$.

15. The method of claim 14, wherein the motor neuron is hypoxic.

16. The method of claim 14, wherein the VEGF-A protein is administered intrathecally.

* * * * *